United States Patent
Lisanti et al.

(10) Patent No.: US 10,085,987 B2
(45) Date of Patent: Oct. 2, 2018

(54) MCT PROTEIN INHIBITOR-RELATED PROGNOSTIC AND THERAPEUTIC METHODS

(71) Applicant: Thomas Jefferson University, Philadelphia, PA (US)

(72) Inventors: Michael P. Lisanti, Manchester (GB); Federica Sotgia, Manchester (GB)

(73) Assignee: THOMAS JEFFERSON UNIVERSITY, Philadelphia, PA (US)

(*) Notice: Subject to any disclaimer, the term of this patent is extended or adjusted under 35 U.S.C. 154(b) by 0 days.

(21) Appl. No.: 14/374,550

(22) PCT Filed: Jan. 25, 2013

(86) PCT No.: PCT/US2013/023209
§ 371 (c)(1),
(2) Date: Jul. 25, 2014

(87) PCT Pub. No.: WO2013/112881
PCT Pub. Date: Aug. 1, 2013

(65) Prior Publication Data
US 2014/0378477 A1 Dec. 25, 2014

Related U.S. Application Data

(60) Provisional application No. 61/591,473, filed on Jan. 27, 2012.

(51) Int. Cl.
*A61K 31/519* (2006.01)
*G01N 33/574* (2006.01)
*G01N 33/68* (2006.01)

(52) U.S. Cl.
CPC ..... *A61K 31/519* (2013.01); *G01N 33/57407* (2013.01); *G01N 33/57492* (2013.01);
(Continued)

(58) Field of Classification Search
USPC ...................................................... 514/260.1
See application file for complete search history.

(56) References Cited

U.S. PATENT DOCUMENTS 4,981,785 A 1/1991 Nayak
5,124,246 A 6/1992 Urdea et al.
(Continued)

FOREIGN PATENT DOCUMENTS

WO 1991013904 A1 1/1991
WO 1997027212 A1 7/1997
(Continued)

OTHER PUBLICATIONS

Ovens et al., Biochem. J., 2010;413:217-225.*
(Continued)

*Primary Examiner* — San Ming R Hui
(74) *Attorney, Agent, or Firm* — Cozen O'Connor

(57) ABSTRACT

This invention provides a method of identifying one or more subgroups of cancer patients that are likely to benefit from treatment with a monocarboxylate transporter (MCT) protein inhibitor comprising: (a) obtaining a sample of a cancer/tumor tissue from each of said cancer patients; (b) determining the expression level of stromal MCT4 protein in each of said samples of cancer/tumor tissue to obtain a first dataset; and (c) using the expression level of the stromal MCT4 protein from said first dataset to classify each of said sets of one or more cancer patients as stromal MCT4-positive or stromal MCT4-negative, wherein the cancer patients classified as stromal MCT4-positive are patients that are more likely to benefit from treatment with said MCT protein inhibitor. This invention also provides related methods for treating a cancer/tumor whose stromal component expresses the MCT4 protein in a patient.

2 Claims, 8 Drawing Sheets

(52) U.S. Cl.
CPC ... *G01N 33/6872* (2013.01); *G01N 2333/705* (2013.01); *G01N 2800/52* (2013.01)

(56) References Cited

U.S. PATENT DOCUMENTS

| | | | |
|---|---|---|---|
| 5,358,691 | A | 10/1994 | Clark et al. |
| 5,359,100 | A | 10/1994 | Urdea et al. |
| 5,545,730 | A | 8/1996 | Urdea et al. |
| 5,571,670 | A | 11/1996 | Urdea et al. |
| 5,580,731 | A | 12/1996 | Chang et al. |
| 5,591,584 | A | 1/1997 | Chang et al. |
| 5,594,117 | A | 1/1997 | Urdea et al. |
| 5,594,118 | A | 1/1997 | Urdea et al. |
| 5,597,909 | A | 1/1997 | Urdea et al. |
| 5,624,802 | A | 4/1997 | Urdea et al. |
| 5,635,352 | A | 6/1997 | Urdea et al. |
| 5,681,697 | A | 10/1997 | Urdea et al. |
| 5,681,702 | A | 10/1997 | Collins et al. |
| 5,693,617 | A | 12/1997 | Stein et al. |
| 5,756,764 | A | 5/1998 | Fenteany et al. |
| 5,780,454 | A | 7/1998 | Adams et al. |
| 5,885,530 | A | 3/1999 | Babson et al. |
| 6,018,020 | A | 1/2000 | Attwood et al. |
| 6,066,730 | A | 5/2000 | Adams et al. |
| 6,075,150 | A | 6/2000 | Wang et al. |
| 6,083,903 | A | 7/2000 | Adams et al. |
| 6,096,778 | A | 8/2000 | Chatterjee et al. |
| 6,147,223 | A | 11/2000 | Fenteany et al. |
| 6,159,750 | A | 12/2000 | Edmonds |
| 6,297,217 | B1 | 10/2001 | Adams et al. |
| 6,310,057 | B1 | 10/2001 | Chatterjee et al. |
| 6,335,358 | B1 | 1/2002 | Fenteany et al. |
| 6,432,662 | B1 | 8/2002 | Davis et al. |
| 6,465,433 | B1 | 10/2002 | Adams et al. |
| 6,548,668 | B2 | 4/2003 | Adams et al. |
| 6,617,317 | B1 | 9/2003 | Adams et al. |
| 6,645,999 | B1 | 11/2003 | Schreiber et al. |
| 6,747,150 | B2 | 6/2004 | Adams et al. |
| 6,781,000 | B1 | 8/2004 | Wang et al. |
| 6,831,099 | B1 | 12/2004 | Crews et al. |
| 2003/0135033 | A1 | 7/2003 | Klippel-Giese et al. |
| 2003/0165895 | A1 | 9/2003 | Czerniak et al. |
| 2003/0166572 | A1 | 9/2003 | Furet et al. |
| 2004/0043004 | A1 | 3/2004 | Bender et al. |
| 2004/0167337 | A1 | 8/2004 | Furet et al. |
| 2004/0186167 | A1 | 9/2004 | Dou et al. |
| 2005/0032135 | A1* | 2/2005 | Zerangue ............ A61K 31/195 435/7.23 |
| 2005/0203162 | A1 | 9/2005 | Xiao et al. |
| 2006/0183141 | A1 | 8/2006 | Chang et al. |
| 2006/0275844 | A1 | 12/2006 | Linke et al. |
| 2006/0281122 | A1 | 12/2006 | Bryant et al. |
| 2007/0020297 | A1 | 1/2007 | Wheeler et al. |
| 2007/0122856 | A1 | 5/2007 | Georges et al. |
| 2008/0064055 | A1 | 3/2008 | Bryant et al. |
| 2008/0138345 | A1 | 6/2008 | De Sauvage et al. |
| 2009/0047215 | A1 | 2/2009 | Harris |
| 2009/0220551 | A1 | 9/2009 | Sampson et al. |
| 2010/0086922 | A1 | 4/2010 | Bryant et al. |
| 2010/0255004 | A1 | 10/2010 | DePinho et al. |
| 2010/0330106 | A1 | 12/2010 | Noguera-Troise et al. |
| 2012/0039805 | A1 | 2/2012 | Lisanti et al. |

FOREIGN PATENT DOCUMENTS

| | | |
|---|---|---|
| WO | 1999030707 A1 | 6/1999 |
| WO | 2002030973 A2 | 4/2002 |
| WO | 2002096933 A1 | 12/2002 |
| WO | 2003018557 A1 | 3/2003 |
| WO | 2004022070 A1 | 3/2004 |
| WO | 2004064755 A2 | 8/2004 |
| WO | 2004065394 A1 | 8/2004 |
| WO | 2004071382 A2 | 8/2004 |
| WO | 2005002572 A2 | 1/2005 |
| WO | 2005003137 A1 | 1/2005 |
| WO | 2005005601 A2 | 1/2005 |
| WO | 2005016859 A2 | 2/2005 |
| WO | 2005021558 A2 | 3/2005 |
| WO | 2005030707 A1 | 4/2005 |
| WO | 2005099687 A2 | 10/2005 |
| WO | 2005105826 A1 | 11/2005 |
| WO | 2005111008 A2 | 11/2005 |
| WO | 2005115431 A2 | 12/2005 |
| WO | 2006045066 A2 | 4/2006 |
| WO | 2008067065 A2 | 6/2008 |
| WO | 2010089580 A1 | 8/2010 |
| WO | 2010096627 A1 | 8/2010 |

OTHER PUBLICATIONS

Sotgia et al., Breast cancer Research, 2011;13:213.*
Sloan EK, Ciocca DR, Pouliot N, Natoli A, Restall C, Henderson MA, Fanelli MA, Cuello-Carrion FD, Gago FE, Anderson RL. Stromal cell expression of caveolin-1 predicts outcome in breast cancer. Am J Pathol 2009; 174:6, 2035-2043.
Sotgia F, Martinez-Outschoorn UE, Pavlides S, Howeli A, Pestell RG, Lisanti MP. Understanding the Warburg effect and the prognostic value of stromal caveolin-1 as a marker of a lethal tumor microenvironment. Breast Cancer Res 2011; 13:213, 1-13.
Sotgia F, Martinez-Outschoorn UE, Howell A, Pestell RG, Pavlides S, Lisanti MP. Caveolin-1 and Cancer Metabolism in the Tumor Microenvironment: Markers, Models, and Mechanisms. Annu Rev Pathol 2012; 7:423-467.
Themeau T, original Splus-> R port by T. Lumley. Survival: Survival analysis, including penalised likelihood. R package version 236-9 2011; http://CRAN.R-project.org/package-survival.
Trimmer C, Sotgia F, Whitaker-Menezes D, Balliet RM, Eaton G, Martinez-Outschoorn UE, Pavlides S, Howell A, Iozzo RV, Pestell RG, Scherer PE, Capozza F, Lisanti MP. Caveolin-1 and mitochondrial SOD2 (MnSOD} function as tumor suppressors in the stromal microenvironment: A new genetically tractable model for human cancer associated fibroblasts. Cancer Biol Ther 2011; 11:4, 383-394.
Ullah MS, Davies AJ, Halestrap AP. The plasma membrane lactate transporter MCT4, but not MCT1, is up-regulated by hypoxia through a HIF-1alpha-dependent mechanism. J Biol Chem 2006; 281:9030-9037.
Vander Heiden MG, Cantley LC, Thompson CB. Understanding the Warburg effect: the metabolic requirements of cell proliferation. Science 2009; 324:1029-33.
Varanasi UR, Car B, Simpson DP. Lactic acidosis associated with metastatic breast carcinoma. Cancer Treat Rep 1980; 64:1283-5.
Walenta S, Salameh A, Lyng H, Evensen JF, Mitze M, Rofstad EK, Mueller-Klieser W. Correlation of high lactate levels in head and neck tumors with incidence of metastasis. Am J Pathol 1997; 150:2. 409-415.
Walenta S, Wetterling M, Lehrke M, Schwickert G, Sundfor K, Rofstad EK, Mueller-Klieser W. High lactate levels predict likelihood of metastases, tumor recurrence, and restricted patient survival in human cervical cancers. Cancer Res 2000; 60:916-921.
Walenta S, Mueller-Klieser WF. Lactate: mirror and motor of tumor malignancy. Semin Radiat Oncol 2004; 14:3, 267-274.
Warburg O. On the origin of cancer cells. Science 1956; 123:309-314.
Warburg O. On respiratory impairment in cancer cells. Science 1956; 124:269-270.
Warner E. Type B lactic acidosis and metastatic breast cancer. Breast Cancer Res Treat 1992; 24:75-79.
Whitaker-Menezes D, Martinez-Outschoorn UE, Lin Z, Ertel A, Flomenberg N, Witkiewicz AK, Birbe RC, Howell A, Pavlides S, Gandara R, Pestell RG, Sotgia F, Philp NJ, Lisanti MP. Evidence for a stromal-epithelial "lactate shuttle" in human tumors: MCT4 is a marker of oxidative stress in cancer-associated fibroblasts. Cell Cycle 2011; 10:11, 1772-1783.
Whitaker-Menezes D, Martinez-Outschoorn UE, Flomenberg N, Birbe RC, Witkiewicz AK, Howell A, Pavlides S, Tsirigos A, Ertel A, Pestell RG, Broda P, Minetti C, Lisanti MP, Sotgia F. Hyperactivation of Oxidative Mitochondrial Metabolism in Epithelial Cancer

(56) References Cited

OTHER PUBLICATIONS

Cells In Situ: Visualizing the Therapeutic Effects of Metformin in Tumor Tissue. Cell Cycle 2011; 10:23. 4047-4064.

Witkiewicz AK, Dasgupta A, Sotgia F, Mercier I, Pestell RG, Sabel M, Kleer CG, Brody JR, Lisanti MP. An absence of stromal caveolin-1 expression predicts early tumor recurrence and poor clinical outcome in human breast cancers. Am J Pathol 2009; 174:6. 2023-2034.

Witkiewicz AK, Dasgupta , Nguyen KH, Liu C, Kovatich AJ, Schwartz GF, Pestell RG, Sotgia F, Rui H, Lisant MP. Stromal caveolin-1 levels predict early DCIS progression to invasive breast cancer Cancer Biol Ther 2009; 8:11, 1071-1079.

Witkiewicz AK, Dasgupta A, Sammons S, Er 0, Potoczek MB, Guiles F, Sotgia F, Brody JR, Mitchell EP, Lisanti MP. Loss of stromal caveolin-1 expression predicts poor clinical outcome in triple negative and basal-like breast cancers. Cancer Biol Ther 2010; 10:2, 135-143.

Witkiewicz AK, Kline J, Queenan M, Brody JR, Tsirigos A, Bilal E, Pavlides S, Ertel A, Sotgia F, Lisanti MP. Molecular profiling of a lethal tumor microenvironment, as defined by stromal caveolin-1 status in breast cancers. Cell Cycle 2011; 10:11, 1794-1809.

Wu KN, Queenan M, Brody JR, Potoczek M, Sotgia F, Lisanti MP, Witkiewicz AK. Loss of stromal caveolin-1 expression in malignant melanoma metastases predicts poor survival. Cell Cycle 2011; 10:24, 4250-4255.

Zu XL, Guppy M. Cancer metabolism: facts, fantasy, and fiction. Biochem Biophys Res Commun 2004; 313:459-465.

Balliet RM, Capparelli C, Guido C, Pestell TG, Martinez-Outschoorn UE, Lin Z, Whitaker-Menezes D, Chiavarina B., Pestell RG, Howell A, Sotgia F, Lisanti MP. Mitochondrial oxidative stress in cancer-associated fibroblasts drives lactate production, promoting breast cancer tumor growth: Understanding the aging and cancer connection. Cell Cycle 2011; 10:23, 4065-4073.

Bergersen LH. Is lactate food for neurons? Comparison of monocarboxylate transporter subtypes in brain and muscle. Neuroscience 2007; 145:11-19.

Bonuccelli G, Whitaker-Menezes D, Castello-Cros R, Pavlides S, Pestell RG, Fatatis A, Witkiewicz AK, Vander Heiden MG, Migneco G, Chiavarina B, Frank PG, Capozza F, Flomenberg N, Martinez-Outschoorn UE, Sotgia F, Lisanti MP. The reverse Warburg effect: Glycolysis inhibitor prevent the tumor promoting effects of caveolin-1 deficient cancer associated fibroblasts. Cell Cycle 2010; 9:10, 1960-1971.

Brizel DM, Schroeder T, Scher RL, Walenta S, Clough RW, Dewhirst MW, Mueller-Klieser W. Elevated tumor lactate concentrations predict for an increased risk of metastases in head-and-neck cancer. Int J Radiat Oncol Biol Phys 2001; 51:2, 349-353.

Brooks GA. Current concepts in lactate exchange. Med Sci Sports Exerc 1991; 23:8, 895-906.

Brooks GA. Lactate shuttles in nature. Biochem Soc Trans 2002; 30:Part 2, 258-264.

Bueno V, Binet I, Steger U, Bundick R, Ferguson D, Murray C, Donald D, Wood K. The specific monocarboxylate transporter (MCT1) inhibitor, AR-C117977, a novel immunosuppressant, prolongs allograft survival in the mouse. Transplantation 2007; 84:1204-1207.

Cheng JC, Esparza SD, Knez VM, Sakamoto KM, Moore TB. Severe lactic acidosis in a 14-year-old female with metastatic undifferentiated carcinoma of unknown primary. J Pediatr Hematol Oncol 2004; 26:11, 780-782.

Chiavarina B, Whitaker-Menezes D, Migneco G, Martinez-Outschoorn UE, Pavlides S, Howell A, Tanowitz HB, Casimiro MC, Wang C, Pestell RG, Grieshaber P, Caro J, Sotgia F, Lisanti MP. HIF1-alpha functions as a tumor promoter in cancer associated fibroblasts, and as a tumor suppressor in breast cancer cells: Autophagy drives compartment-specific oncogenesis. Cell Cycle 2010; 9:17, 3534-3551.

Chiavarina B, Whitaker-Menezes D, Martinez-Outschoorn UE, Witkiewicz AK, Birbe RC, Howell A, Pestell RG, Smith J, Daniel R, Sotgia F, Lisanti MP. Pyruvate kinase expression (PKMI and PKM2) in cancer-associated fibroblasts drives stromal nutrient production and tumor growth. Cancer Biol Ther 2011; 12:12, 1101-1113.

Dimmer KS, Friedrich B, Lang F, Deitmer JW, Broer S. The low-affinity monocarboxylate transporter MCT4 is adapted to the export of lactate in highly glycolytic cells. Biochem J 2000; 350 Pt 1:219-227.

Di Vizio D, Morello M, Sotgia F, Pestell RG, Freeman MR, Lisanti MP. An absence of stromal caveolin-1 is associated with advanced prostate cancer, metastatic disease and epithelial AKT activation. Cell Cycle 2009; 8:15, 2420-2424.

El-Gendi SM, Mostafa MF, El-Gendi AM. Stromal Caveolin-1 Expression in Breast Carcinoma. Correlation with Early Tumor Recurrence and Clinical Outcome. Pathol Oncol Res 2012, 18:459-469; DOI 10.1007/sI2253-011-9469-5: In Press.

Ertel A, Tsirigos A, Whitaker-Menezes D, Birbe RC, Pavlides S, Martinez-Outschoorn UE, Pestell RG, Howell A, Sotgia F, Lisanti MP. Is cancer a metabolic rebellion against host aging? In the quest for immortality, tumor cells try to save themselves by boosting mitochondrial metabolism. Cell Cycle 2012; 11:2, 253-263.

Evans TR, Stein RC, Ford HT, Gazet JC, Chamberlain GV, Coombes RC. Lactic acidosis. A presentation of metastatic breast cancer arising in pregnancy. Cancer 1992; 69:2, 453-456.

Gallagher SM, Castorino JJ, Wang D, Philp NJ. Monocarboxylate transporter 4 regulates maturation and trafficking of CD147 to the plasma membrane in the metastatic breast cancer cell line MDA-MB-231. Cancer Res 2007; 67:4182-9.

Hart IR, Fidler IJ. Role of organ selectivity in the determination of metastatic patterns of B16 melanoma. Cancer Res 1980; 40:2281-7.

Hart IR. 'Seed and soil' revisited: mechanisms of site-specific metastasis. Cancer Metastasis Rev 1982; 1:5-16.

Ko YH, Lin Z, Flomenberg N, Pestell RG, Howell A, Sotgia F, Lisanti MP, Martinez-Outschoorn UE. Glutamine fuels a vicious cycle of autophagy in the tumor stroma and oxidative mitochondrial metabolism in epithelial cancer cells: Implications for preventing chemotherapy resistance. Cancer Biol Ther 2011; 12:12, 1085-1097.

Koo JS, Park S, Kim SI, Lee S, Park BW. The impact of caveolin protein expression in tumor stroma on prognosis of breast cancer. Tumour Biol 2011; 32:787-799.

Lisanti MP, Martinez-Outschoorn UE, Pavlides S, Whitaker-Menezes D, Pestell RG, Howell A, Sotgia F. Accelerated aging in the tumor microenvironment: connecting aging, inflammation and cancer metabolism with personalized medicine. Cell Cycle 2011; 10:13, 2059-2063.

Lisanti MP, Martinez-Outschoorn UE, Lin Z, Pavlides S, Whitaker-Menezes D, Pestell RG, Howell A Sotgia F. Hydrogen peroxide fuels aging, inflammation, cancer metabolism and metastasis: the seed and soil also needs "fertilizer". Cell Cycle 2011; 10:15, 2440-2449.

Magistretti PJ, Pellerin L. The contribution of astrocytes to the 18F-2-deoxyglucose signal in PET activation studies. Mol Psychiatry 1996; 1:445-52.

Magistretti PJ. Neuron-glia metabolic coupling and plasticity. J Exp Biol 2006; 209:2304-11.

Magistretti PJ. Role of glutamate in neuron-glia metabolic coupling. Am J Clin Nutr 2009; 90:875S-80S.

Martinez-Outschoorn UE, Whitaker-Menezes D, Pavlides S, Chiavarina B, Bonuccelli G, Casey T, Tsirigos A, Migneco G, Witkiewicz A, Balliet R, Mercier I, Wang C, Flomenberg N, Howell A, Lin Z, Caro J, Pestell RG, Sotgia F, Lisanti MP. The autophagic tumor stroma model of cancer or "battery-operated tumor growth": A simple solution to the autophagy paradox. Cell Cycle 2010; 9:21, 4297-4306.

Martinez-Outschoorn UE, Pavlides S, Whitaker-Menezes D, Daumer KM, Milliman JN, Chiavarina B, Migneco G, Witkiewicz AK, Martinez-Cantarin MP, Flomenberg N, Howell A, Pestell RG, Lisanti MP, Sotgia F. Tumor cells induce the cancer associated fibroblast phenotype via caveolin-1 degradation: Implications for breast cancer and DCIS therapy with autophagy inhibitors. Cell Cycle 2010; 9:12, 2423-2433.

Martinez-Outschoorn UE, Balliet RM, Rivadeneira DB, Chiavarina B, Pavlides S, Wang C, Whitaker-Menezes D, Daumer KM, Lin Z,

(56) References Cited

OTHER PUBLICATIONS

Witkiewicz AK, Flomenberg N, Howell A, Pestell RG, Knudsen ES, Sotgia F, Lisanti MP. Oxidative stress in cancer associated fibroblasts drives tumor-stroma co-evolution: A new paradigm for understanding tumor metabolism, the field effect and genomic instability in cancer cells. Cell Cycle 2010; 9:16, 3256-3276.

Martinez-Outschoorn UE, Trimmer C, Lin Z, Whitaker-Menezes D, Chiavarina B, Zhou J, Wang C, Pavlides S, Martinez-Cantarin MP, Capozza F, Witkiewicz AK, Flomenberg N, Howell A, Pestell RG, Caro J, Lisanti MP, Sotgia F. Autophagy in cancer associated fibroblasts promotes tumor cell survival: Role of hypoxia, HIF1 induction and NFkappaB activation in the tumor stromal microenvironment. Cell Cycle 2010; 9:17, 3515-3533.

Martinez-Outschoorn UE, Pestell RG, Howell A, Nagajyothi F, Machado FS, Tanowitz HB, Sotgia F, Lisanti MP. Energy transfer in "parasitic" cancer metabolism: Mitochondria are the powerhouse and Achilles' heel of tumor cells. Cell Cycle 2011; 10:24, 4208-4216.

Martinez-Outschoorn UE, Pavlides S, Howell A, Pestell RG, Tanowitz HB, Sotgia F, Lisanti MP. Stromal-epithelial metabolic coupling in cancer: integrating autophagy and metabolism in the tumor microenvironment. Int J Biochem Cell Biol 2011; 43:1045-1051.

Martinez-Outschoorn UE, Lin Z, Trimmer C, Flomenberg N, Wang C, Pavlides S, Pestell RG, Howell A, Sotgia F, Lisanti MP. Cancer cells metabolically "fertilize" the tumor microenvironment with hydrogen peroxide, driving the Warburg effect: Implications for PET imaging of human tumors. Cell Cycle 2011; 10:15, 2504-2520.

Martinez-Outschoorn UE, Whitaker-Menezes D, Lin Z, Flomenberg N, Howell A, Pestell RG, •Lisanti MP, Sotgia F. Cytokine production and inflammation drive autophagy in the tumor microenvironment: role of stromal caveolin-1 as a key regulator. Cell Cycle 2011; 10:11, 1784-1793.

Martinez-Outschoorn UE, Prisco M, Ertel, A, Tsirigos, Lin, Z, Pavlides, S, Wang, C, Flomenberg, N, Knudsen, ES, Howell, A, Pestell, RG, Sotgia,F, Lisanti, MP, Ketones and lactate increase cancer cell "sternness", driving recurrence, metastasis and poor clinical outcome in breast cancer, Achieving personalized medicine via metabolo-genomics, Cell Cycle 2011; 10:8, 1271-1286.

Martinez-Outschoorn UE, Goldberg A, Lin Z, Ko YH, Flomenberg N, Wang C., Pavlides S, Pestell RG, Howell A, Sotgia F, Lisanti MP, Anti-estrogen resistance in breast cancer is induced by the tumor microenvironment and can be overcome by inhibiting mitochondrial function in epithelial cancer cells. Cancer Biol Ther 2011; 12:10, 924-938.

Martinez-Outschoorn UE, Lin Z, Ko YH, Goldberg AF, Flomenberg N, Wang C, Pavlides S, Pestell RG, Howell A, Sotgia F, Lisanti MP. Understanding the metabolic basis of drug resistance: Therapeutic induction of the Warburg effect kills cancer cells. Cell Cycle 2011; 10:15, 2521-2528.

Martinez-Outschoorn UE, Sotgia F, Lisanti MP. Power Surge: Supporting Cells "Fuel" Cancer Cell Mitochondria. Cell Metab 2012; 15:4-5.

McConnell AA, Parfitt VL, Walker PR. An unusual case of shock in a young woman. Postgrad Med J 1989; 65:120.

Ovens MJ, Davies AJ, Wilson MC, Murray CM, Halestrap AP. AR-C155858 is a potent inhibitor of monocarboxylate transporters MCTI and MCT2 that binds to an intracellular site involving transmembrane helices 7-10. Biochem J 2010; 425:523-30.

Paget S. The distribution of secondary growths in cancer of the breast. 1889. Cancer Metastasis Rev 1989; 8:98-101.

Pavlides S, Whitaker-Menenes D, Castello-Cros R, Flomenberg N, Witkiewicz AK, Frank PG, Casimiro MC, Wang C, Fortina P, Addya S, Pestell RG, Martinez-Outschoorn UE, Sotgia F, Lisanti MP. The reverse Warburg effect: aerobic glycolysis in cancer associated fibroblasts and the tumor stroma. Cell Cycle 2009; 8:23, 3984-4001.

Pavlides S, Tsirigos A, Vera I. Flomenberg N, Frank PG, Casimiro MC, Wang C, Fortina P, Addya S, Pestell RG, Martinez-Outschoorn UE, Sotgia F, Lisanti MP. Loss of stromal caveolin-1 leads to oxidative stress, mimics hypoxia and drives inflammation in the tumor microenvironment, conferring the "reverse Warburg effect": A transcriptional informatics analysis with validation. Cell Cycle 2010; 9:11, 2201-2219.

Pavlides S, Tsirigos A, Migneco G, Whitaker-Menezes D, Chiavarina B, Flomenberg N, Frank PG, Casimiro MC, Wang C, Pestell RG, Martinez-Outschoorn UE, Howell A, Sotgia F, Lisanti MP. The autophagic tumor stroma model of cancer: Role of oxidative stress and ketone production in fueling tumor cell metabolism. Cell Cycle 2010; 9:17, 3485-3505.

Pavlides S, Vera I, Gandara R, Sneddon S, Pestell RG, Mercier I, Martinez-Outschoorn UE, Whitaker-Menezes D, Howell A, Sotgia F, Lisanti MP. Warburg Meets Autophagy: Cancer-Associated Fibroblasts Accelerate Tumor Growth and Metastasis via Oxidative Stress, Mitophagy, and Aerobic Glycolysis. Antioxid Redox Signal 2012, 16:11, 1264-1284.

Pertega-Gomes N, Vizcaino JR, Miranda-Goncalves V, Pinheiro C, Silva J, Pereira H, Monteiro P, Henrique R , Reis RM, Lopes C, Baltazar F. Monocarboxylate transporter 4 (MCT4) and CD147 overexpression is associated with poor prognosis in prostate cancer. BMC Cancer 2011;11:312, 1-9.

Pierre K, Pellerin L. Monocarboxylate transporters in the central nervous system: distribution, regulation and function. J Neurochem 2005; 94: 1-14.

Qian N, Ueno T, Kawaguchi-Sakita N, Kawashima M, Yoshida N, Mikami Y, Wakasa T, Shintaku M, Tsuyuki S, Inamoto T, Toi M. Prognostic significance of tumor/stromal caveolin-1 expression in breast cancer patients. Cancer Sci 2011; 102:8, 1590-1596.

R-Development-Core-Team. R: A language and environment for statistical computing. R Foundation for Statistical Computing, Vienna, Austria 2011; ISBN 3-900051-07-0. http://www.R-project.org.

Sculier JP, Nicaise C, Klastersky J. Lactic acidosis: a metabolic complication of extensive metastatic cancer. Eur J Cancer Clin Oncol 1983; 19:5, 597-601.

Simpkins S, Holliday D, Speirs V. The role of stromal caveolin-1 in breast cancer progression. NCRI Cancer Conference 2011; Abstract #A222:http://www.neri.org.uk/ nericonference/2011abstracts/abstracts/A222.html.

Oikawa, et al., "Angiogenic activity of rat mammary carcinomas induced by 7,12-dimethylbenz[a]anthracene and its inhibition by medroxyprogesterone acetate: possible involvement of antiangiogenic action of medroxyprogesterone acetate in its tumor growth inhibition", Cancer Letters, vol. 43, pp. 85-92, 1988.

O'Reilly, M.S., et al., "Angiostatin: A novel angiogenesis inhibitor that mediates the suppression of metastases by a lewis lung carcinoma", Cell, vol. 79, No. 2, pp. 315-328, 1994.

Ovens, M.J., et al., "The inhibition of monocarboxylate transporter 2 (MCT2) by AR-C155858 is modulated by the associated ancillary protein", Biochem. J., vol. 431, pp. 217-225, 2010.

Parat, M.O., et al., "Caveolin-1, caveolae, and gliboblastoma", Neuro Oncol, vol. 14, No. 6, pp. 679-688, 2012.

Park, J., et al., "RNA interference-directed caveolin-1 knockdown sensitizes SNI2CPM6 cells to doxorubicin-induced apoptosis and reduces lung metastasis", Tumour Biol, vol. 31, pp. 643-650, 2010.

Parton, R.G., et al., "The multiple faces of caveolae", Nat Rev Mol Cell Biol, vol. 8, pp. 185-194, 2007.

Patel, H.H., et al., "Caveolae as organizers of pharmacologically relevant signal transduction molecules", Annual Review of Pharmacology and Toxicology, vol. 48, pp. 359-391, 2008.

Pepe, M.S., et al., "Limitations of the odds ratio in gaugin the performance of a diagnostic, prognostic, or screening marker", American Journal of Epidemiology, vol. 159, No. 9, pp. 882-890, 2004.

Perrone, G., et al., "COX-2 localization within plasma membrane caveolae-like structures in human lobular intrapeithelical neoplasia of the breast", Virchows Archiv: an international journal of pathology, vol. 451, No. 6, pp. 1039-1045, 2007.

Peterson, O.W., et al., "Epithelial to mesenchymal transition in human breast cancer can provide a nonmalignant stroma", Am J Pathol, vol. 162, pp. 391-402, 2003.

Picardo, M., et al., "Migration stimulating activity in serum of breast cancer patients", Lancet, vol. 337, pp. 130-133, 1991.

(56) References Cited

OTHER PUBLICATIONS

Quann, K., et al., "Caveolin-1 is a negative regulator of tumor growth in glioblastoma and modulates chemosensitivity to temozolomide", Cell Cycle, vol. 12, No. 10, pp. 1510-1520, 2013.
Racker, E., et al., "Glycolysis and methylaminoisobutyrate uptake in rat-1 cells transfected with ras or myc oncogenes", Proc Natl Acad Sci USA, vol. 82, pp. 3535-3538, 1985.
Razani, B., et al., "Caveolae: from cell biology to animal physiology", Pharmacological Reviews, vol. 54, pp. 431-467, 2002.
Reunanen, N. et al., "Enhancement of fibroblast collagenase (matrix metalloproteinase-1)gene expression by ceramide is mediated by extracellular signal-regulated and stress-activated protein kinase pathways", J Biol Chem, vol. 273, pp. 5237-5145, 1998.
Ronnov-Jessen, L., et al., "Induction of alpha-smooth muscle actin by transforming growth factor-beta 1 in quiescent human breast gland fibroblasts. Implications for myofibroblast generation in breast neoplasia", Lab Invest, vol. 68, pp. 696-707, 1993.
Ronnov-Jessen, L., et al., "Cellular changes involved in conversion of normal to malignant breast: importance of the stromal reaction." Physiol Rev, vol. 76, pp. 69-125, 1996.
Rydzewski, R.M., et al., "Optimization of Subsite Binding to the β5 Subunit of the Human 20S Proteasome Using Vinyl Sulfones and 2-Keto-1,3,4-oxadiazoles: Syntheses and Cellular Properties of Potent, Selective Proteasome Inhibitors", Journal of Medicinal Chemistry, vol. 49, No. 10, pp. 2953-2968, 2006.
Sagara, Y., et al., "Clinical significance of caveolin-1, caveolin-2 and HER2/neu mRNA expression in human breast cancer", British Journal of Cancer, vol. 91, No. 5, pp. 959-965, 2004.
Sakr, R., et al., "Ductal carcinoma in situ: Value of sentinel lymph node biopsy", Journal of Surgical Oncology, vol. 94, pp. 426-430, 2006.
Salerno, M., et al., "Inhibition of signal transduction by the nm23 metastasis suppressor: Possible mechanisms", Clinical & Experimental Metastasis, vol. 20, No. 1, pp. 3-10, 2003.
Santos, A.M., et al., "Targeting fibroblast activation protein inhibits tumor stromagenesis and growth in mice.", J Clin Invest, vol. 119, pp. 3613-3625, 2009.
Savage, K., et al., "Caveolin 1 is overexpressed and amplified in a subset of basal-like and metaplastic breast carcinomas: A morphologic, ultrastructural, immunohistochemical, and in situ hybridization analysis", Clinical Cancer Research, vol. 13, No. 1, pp. 90-101, 2007.
Schmitz, M., et al., "Effect of cavtratin, a caveolin-1 scaffolding domain peptide, on oligodendroglial signaling cascades", Cellular and Molecular Neurobiology, vol. 31, pp. 991-997, 2011.
Schor, A.M., et al., "Phenotypic heterogeneity in breast fibroblasts: functional anomaly in fibroblasts from histologically normal tissue adjacent to carcinoma", Int J Cancer, vol. 59, pp. 25-32, 1994.
Schor, S.L., et al., "Occurrence of a fetal fibroblast phenotype in familial breast cancer", Int J Cancer, vol. 37, pp. 831-836, 1986.
Schor, S.L., et al., "Hypothesis: persistent expression of fetal phenotypic characteristics by fibroblasts is associated with an increased susceptibility to neoplastic disease", Exp Cell Biol, vol. 55, pp. 11-17, 1987.
Schor, S.L., et al., "Foetal-to-adult transitions in fibroblast phenotype: their possible relevance to the pathogenesis of cancer", J Cell Sci Suppl, vol. 8, pp. 165-180, 1987.
Schor, S.L., et al., "Foetal and cancer patient fibroblasts produce an autocrine migration-stimulating factor not made by normal adult cells", J Cell Sci, vol. 90 (Pt 3), pp. 391-399, 1988.
Schor, S.L., et al., "Fibroblasts from cancer patients display a mixture of both foetal and adult-like phenotypic characteristics", J Cell Sci, vol. 90 (Pt 3), pp. 401-407, 1988.
Schor, S.L., et al., "Mechanism of action of the migration stimulating factor produced by fetal and cancer patient fibroblasts: effect on hyaluronic and synthesis", In Vitro Cell Dev Biol, vol. 25, pp. 737-746, 1989.
Schor, S.L., et al., "Characterization of migration-stimulating factor (MSF): evidence for its role in cancer pathogenesis", Cancer Invest, vol. 8, pp. 665-667, 1990.
Schor, S.L., et al., "Heterogeneity amongst fibroblasts in the production of migration stimulating factor (MSF): Implications for cancer pathogenesis", Exs, vol. 59, pp. 127-146, 1991.
Schor, S.L., et al., "Migration stimulating factor (MSF): its structure, mode of action and possible function in health and disease", Symp Soc Exp Biol, vol. 47, pp. 235-251, 1993.
Schor, S.L., et al., "Fetal-like fibroblasts: their production of migration-stimulating factor and role in tumor progression", Cancer Treat Res, vol. 71, pp. 277-298, 1994.
Schor, S.L., "Fibroblast subpopulations as accelerators of tumor progression: the role of migration stimulating factor", Exs, vol. 74, pp. 273-296, 1995.
Schor, S.L., et al., "Phenotypic and genetic alterations in mammary stroma: implications for tumour progression", Breast Cancer Res, vol. 3, pp. 373-379, 2001.
Schor, S.L., et al., "Migration-stimulating factor: a genetically truncated onco-fetal fibronectin isoform expressed by carcinoma and tumor-associated stromal cells", Cancer Res, vol. 63, pp. 8827-8836, 2003.
Senetta, R., et al., "Caveolin 1 expression independently predicts shorter survival in oligodendrogliomas", J Neuropathol Exp Neurol, vol. 68, pp. 425-431, 2009.
Shetty, P., et al., "Urokinase expression by tumor suppressor protein p53: a novel role in mRNA turnover", American Journal of Respiratory Cell and Molecular Biology, vol. 39, pp. 364-372, 2008.
Sieweke, M.H., et al., "Mediation of wound-related Rous sarcoma virus tumorigenesis by TGF-beta", Science, vol. 248, 1656-1660, 1990.
Sieweke, M.H., et al., "The tumor-promoting effect of wounding: a possible role for TGF-beta-induced stromal alterations", Crit Rev Oncog, vol. 5, pp. 297-311, 1994.
Solinas, G., et al., "Tumor-Conditioned Macrophages Secrete Migration-Stimulating Factor: A New Marker for M2-Polarization, influencing Tumor Cell Motility", The Journal of Immunology, vol. 185, pp. 642-652, 2010.
Spaltenstein, A., et al., "Design and synthesis of novel protease inhibitors. Tripeptide α',β'-epoxyketones as nanomolar inactivators of the proteasome", Tetrahedron Letters, vol. 37, No. 9, 1343-1346, 1996.
Stupp, R., et al., Effects of radiotherapy with concomitant and adjuvant temozolomide versus radiotherapy alone on survival in glioblastoma in a randomised phase III study: 5-year analysis of the EORTC-NCIC trial, Lancet Oncol, vol. 10, pp. 459-466, 2009.
Subramanian, A., et al., "Gene set enrichment analysis: a knowledge-based approach for interpreting genome-wide expression profiles", Proc Natl Acad Sci USA, vol. 102, pp. 15545-15550, 2005.
Sun, Y., et al., p53 down-regulates human matrix metalloproteinase-1 (Collagenase-1) gene expression, J Biol Chem, vol. 274, pp. 11535-11540, 1999.
Sunayama, J., et al., "Crosstalk between the pI3K/mTOR and MEK/ERK pathways involved in the maintenance of self-renewal and tumorigenicity of glioblastoma stem-like cells", Stem Cells, vol. 28, pp. 1930-1939, 2010.
Surowiak, P., et al., "Occurrence of stromal myofibroblasts in the invasive ductal breast cancer tissue is an unfavourable prognostic factor", Anticancer Res, vol. 27, pp. 2917-2924, 2007.
Torres, V.A., et al., "Caveolin-1 controls cell proliferation and cell death by suppressing expressin of the inhibitor of apoptosis protein survivin", Journal of Cell Science, vol. 119, pp. 1812-1823, 2006.
Abulrob, A., et al., "Interactions of EGFR and Caveolin-1 in Human Glioblastoma Cells: Evidence that Tyrosine Phosphorylation regulates EGFR association with caveolae", Oncogene, vol. 23, pp. 6967-6979, 2004.
Anderson, R.L., et al., "Stromal expression of caveolin-1 regulates breast cancer progression", Journal of Bone and Mineral Research, vol. 19, No. 9, p. 1580, Sep. 2004.
Ashburner, M., et al., "Gene Ontology: Tool for the Unification of Biology. The Gene Ontology Consortium", Nature Genetics, vol. 25, pp. 25-29, 2000.
Barresi, V., et al., "Caveolin-1 Expression in Diffuse Gliomas: Correlation with the Proliferation Index, Epidermal Growth Factor Receptor, p53, and 1p/19q status", Hum Pathol, vol. 40, pp. 1738-1746, 2009.

(56) References Cited

OTHER PUBLICATIONS

Beckner, M.E., et al., "Identification of ATP Citrate Lyase as a Positive Regulator of Glycolytic Function in Glioblastomas", International Journal of Cancer, vol. 126, No. 10, pp. 2282-2295, May 15, 2010.

Bogyo, M., et al., "Covalent modification of the active site threonine of proteasomal β subunits and the *Escherichia coli* homolog HsIV by a new class of inhibitors", Proc. Natl. Acad. Sci. vol. 94, 6629-6634, 1997.

Boring, C.C., et al., "Cancer statistics, 1993", CA Cancer J Clin, 1993, vol. 43, pp. 7-26.

Bouget, K., et al., "Hydrazino-aza and N-azapeptoids with therapeutic potential as anticancer agents", Bioorg. Med. Chem., vol. 11, pp. 4881-4889, 2003.

Brada, M., et al., "Multicenter Phase II Trial of Temozolomide in Patients with Glioblastoma Multiforme at First Relapse", Annals of Oncology, vol. 12, pp. 259-266, 2001.

Brennan, et al., "Contribution of DNA and tissue microarray technology to the identification and validation of biomarkers and personalized medicine in breast cancer", Cancer Genomics & Proteomics, vol. 4, pp. 121-134, 2007.

Bruyere, C., et al., "Temozolomide modifies caveolin-1 expression in experimental malignant gliomas in vitro and in vivo", Translational Oncology, vol. 4, pp. 92-100, 2011.

Buckner, J.C., et al., "Central Nervous System Tumors", Mayo Clin Proc, vol. 82, pp. 1271-1286, 2007.

Burgermeister, E., et al., "Caveats of caveolin-1 in cancer progression", Cancer Letters, vol. 268, No. 2, pp. 187-201, Sep. 18, 2008.

Cameron, A.W., et al., "Caveolin-1 Expression is Maintained in Rat and HumanAstroglioma Cell Lines", Gilia, vol. 37, pp. 275-290, 2002.

Carito, V., et al., "Metabolic Remodeling of the Tumor Microenvironment: Migration Stimulating Factor (MSF) Reprograms Myofibroblasts toward Lactate Production, fueling Anabolic Tumor Growth", Cell Cycle, vol. 11, No. 18, pp. 3403-3414, 2012.

Casey, T.M., et al., "Cancer associated fibroblasts stimulated by transforming growth factor beta 1 (TGF-beta 1) increase invasion rate of tumor cells: a population study", Breast Cancer Res Treat, vol. 110, pp. 39-49, 2008.

Cassoni, P., et al., "Caveolin-1 Expression is Variably Displayed in Astroglial-Derived Tumors and Absent in Oligodendrogliomas: Concrete Premises for a New Reliable Diagnostic Marker in Gliomas", Am J Surg Pathol, vol. 31, pp. 760-769, 2007.

Chen, C., et al., "Gene expression profiling identifies genes predictive of oral squamous cell carcinoma", Cancer Epidemiology Biomarkers & Prevention, vol. 17, No. 8, pp. 2152-2162, Aug. 2008.

Christofk, H.R., et al., "Pyruvate kinase M2 is a phosphotyrosine-binding protein", Nature 452, pp. 181-186, 2008.

Christofk, H.R., et al., "The M2 splice isoform of pyruvate kinase is important for cancer metabolism and tumour growth", Nature, vol. 452, pp. 230-233, 2008.

Cohen, A.W., et al., "Caveolin-1 Null Mice Develop Cardiac Hypertrophy with Hyperactivation of p42/44 MAP Kinase in Cardiac Fibroblasts", Am J Physiol Cell Physiol, vol. 284, pp. C457-C474, 2003.

Colletta, A.A., et al., "Anti-oestrogens induce the secretion of active transforming growth factor beta from human fetal fibroblasts", Br J Cancer, vol. 62, pp. 405-409, 1990.

Cosset, E.C., et al., "Involvement of the TGFbeta Pathway in the Regulation of Alpha5 Beta1 Integrins by Caveolin-1 in Human Glioblastoma", International Journal of Cancer, vol. 131, pp. 601-611, 2012.

Daly, M.B., "Tamoxifen in ductal carcinoma in situ", Seminars in Oncology, vol. 33, pp. 647-649, Dec. 2006.

Deeken, J.F., et al., "The blood-brain barrier and cancer: transporters, treatment, and Trojan horses", Clin Cancer Res, vol. 13, pp. 1663-1674, 2007.

Deffieu, M., et al., "Glutathione participates in the regulation of mitophagy in yeast", Journal of Biological Chemistry, vol. 284, No. 22, pp. 14828-14837, 2009.

Desmouliere, A., et al., "Transforming growth factor-beta 1 induces alpha-smooth muscle action expression in granulation tissue myofibroblasts and in quiescent and growing cultured fibroblasts", J Cell Biol, vol. 122, pp. 103-111, 1993.

Direkze, N.C., et al., "Bone marrow contribution to tumor-associated myofibroblasts and fibroblasts", Cancer Res, vol. 64, pp. 8492-8495, 2004.

Ellis I., et al., "Antagonistic effects of TGF-beta 1 and MSF on fibroblast migration and hyaluronic acid synthesis. Possible implications for dermal wound healing", J Cell Sci, vol. 102 (Pt 3), pp. 447-456, 1992.

Engelman, J.A., et al., "Caveolin-mediated regulation of signaling along the p42/44 MAP kinase cascade in vivo. A role for the caveolin-scaffolding domain", FEBS letters, vol. 428, Issue 3, pp. 205-211, 1998.

Engelman, J.A., et al., "Reciprocal regulation of Neu tyrosine kinase activity and caveolin-1 protein expression in vitro and in vivo", The Journal of Biological Chemistry, vol. 273, No. 32, pp. 20448-20455, 1998.

Esteva, F.J., et al., "Integration of systemic chemotherapy in the management of primary breast cancer", The Oncologist, vol. 3, pp. 300-313, 1998.

Feng, S., et al., "Caveolin-1 gene silencing promotes the activation of PI3K/AKT dependent on Eralpha36 and the transformation of MCF10ACE", Science China Life Sciences, vol. 53, pp. 598-605, 2010.

Fenteany, G., et al., "A beta-lactone related to lactacystin induces neurite outgrowth in a neuroblastoma cell line and inhibits cell cycle progression in an osteosarcoma cell line", Proc. Natl. Acad. Sci. USA, vol. 91, No. 8, pp. 3358-3362, 1994.

Fisher, B., et al., "Tamoxifen in the treatment of intraductal breast cancer: National surgical adjuvant breast and bowel project B-24 randomised controlled trial", The Lancet, vol. 353, pp. 1993-2000, Jun. 1999.

Forget, M.A., et al., "The expression of rho proteins decreases with human brain tumor progression: potential tumor markers", Clinical & Experimental Metastasis, vol. 19, pp. 9-15, 2002.

Frank, R., et al., "Clinical biomarkers in drug discovery and development", Nature Reviews, vol. 2, pp. 566-580, 2003.

Fry, D.W., et al., "Specific inhibition of cyclin-dependent kinase 4/6 by PD 0332991 and associated antitumor activity in human tumor xenografts", Mol Cancer Ther, vol. 3, pp. 1427-1438, 2004.

Furuta, E., et al., "Metabolic Genes in Cancer: Their Roles in Tumor Progression and Clinical Implications", Biochim Biophys Acta, vol. 1805, No. 2, pp. 141-152, 2010.

Garcia, S., et al., "Poor prognosis in breast carcinomas correlates with increased expression of targetable CD146 and c-Met and with proteomic basal-like phenotype", Human Pathology, vol. 38, pp. 830-841, 2007.

Garcia-Cardena, G., et al., "Dissecting the interaction between nitric oxide synthase (NOS) and caveolin. Functional significance of the nos caveolin binding doman in vivo", J Biol Chem, vol. 272, No. 41, pp. 25437-25440, 1997.

Goetz, J.G., "Caveolin-1 in tumor progression: the good, the bad and the ugly", Cancer Metastasis Rev, vol. 27, pp. 715-735, 2008.

Grey, A.M., et al., "Purification of the migration stimulating factor produced by fetal and breast cancer patient fibroblasts", Proc Natl Acad Sci, vol. 86, pp. 2438-2442, 1989.

Guo, Z., et al., "Expression and clinical significance of multidrug resistance proteins in brain tumors", Journal of Experimental & Clinical Cancer Research, vol. 29, No. 1, 122 (6 pages).

Haggie, J.A., et al., "Fibroblasts from relatives of patients with hereditary breast cancer show fetal-like behaviour in vitro", Lancet, vol. 1, pp. 1455-1457, 1987.

Han, F., et al., "Caveolin-1 acts as a tumor suppressor by down-regulating epidermal growth factor receptor-mitogen-activated protein kinase signaling pathway in pancreatic carcinoma cell lines", Pancreas, vol. 38, pp. 766-774, 2009.

Han, F., et al., "Caveolin-1 regulating the invasion and expression of matrix metalloproteinase (MMPs) in pancreatic carcinoma cells", The Journal of Surgical Research, vol. 159, pp. 443-450, 2010.

(56) References Cited

OTHER PUBLICATIONS

Haraguchi, M., et al., "Sensitivity of Human KB Cells Expressing Platelet-derived Endothelial Cell Growth Factor to Pyrimidine Antimetabolites", Cancer Res., vol. 53, pp. 5680-5682, 1993.
Heasman, S.J., et al., "GTPases: new insights into their functions from in vivo studies", Nat Rev Mol Cell Biol 2008, vol. 9, pp. 690-701.
Heid, C.A., et al., "Real time quantitative PCT", Genome Res., vol. 6, No. 10, pp. 986-994, 1996.
Toullec, A., et al., Oxidative stress promotes myofibroblast differentiation and tumour spreading, EMBO Mol Med, vol. 2, pp. 211-230, 2010.
Tsujino, T., et al., "Stromal myofibroblasts predict diseases recurrence for colorectal cancer", Clin Cancer Res, vol. 13, pp. 2082-2090, 2007.
Van Deurs, B., et al., "Caveolae: anchored, multifunctional platforms in the lipid ocean", Trends in Cell Biology, vol. 13, pp. 92-100, 2003.
Vozenin-Brotons, M.C., et al., "Antifibotic action of Cu/Zn SOD is mediated by TGF-beta 1 repression and phenotype reversion of myofibroblasts", Free Radic Biol Med, vol. 30, pp. 30-42, 2001.
Waghray, M., et al., "Hydrogen peroxide is a diffusible paracrine signal for the induction of epithelial cell death by activated myofibroblasts", FASEB J, vol. 19, pp. 854-856, 2005.
Walenta, S., et al., "Correlation of high lactate levels in head and neck tumors with incidence of metastasis", Am J Pathol, vol. 150, No. 2, pp. 409-415, 1997.
Williams, T.M., et al., "Caveolin-1 gene disruption promotes mammary tumorigenesis and dramatically enhances long metastasis in vivo. Role of Cav-1 in cell invasiveness and matrix metalloproteinase (MMP-2/9) secretion", J Biol Chem, vol. 279, No. 49, pp. 51630-51646, 2004.
Williams, T.M., et al., "Caveolin-1 in oncogenic transformation, cancer, and metastasis", Am J Physiol Cell Physiol, vol. 288, pp. C494-0506, 2005.
Witkiewicz, A.K., et al., "Loss of Caveolin-1 Expression in Breast Cancer Associated Fibroblasts Correlates with Tumor Aggressiveness", Laboratory Investigation, vol. 89, Supplement, pp. 74A-75A, 2009.
Witkiewicz, A.K., et al., "Towards a new 'stroma-based' classification system for human breast cancer prognosis and therapy", Cell Cycle, vol. 8, No. 11, pp. 1654-1658, 2009.
Witkiewicz, A.K., et al., "Molecular profiling of a lethal tumor microenvironment, as defined by stromal caveolin-1 status in breast cancers", Cell Cycle, vol. 10, No. 11, pp. 1794-1809, 2011.
Xia, H., "Pathologic caveolin-1 regulation of PTEN in idiopathic pulmonary fibrosis", Am J Pathol, vol. 176, pp. 2626-2637, 2010.
Yamamoto, Y., et al., "Combination effect of an angiogenesis inhibitor AGM-1470 with 5'-deoxy-5-fluorouridine, and with hormonal drugs in DMBA-induced rat mammary-tumors", Oncology Reports, vol. 2, No. 5, pp. 793-796, 1995.
Yancy, H.F., et al., "Metastatic Progression and Gene Expression Between Breast Cancer Cell Lines from African American and Caucasian Women", Journal of Carcinogenesis, Biomed Central, vol. 6, No. 8, pp. 1-12, May 1, 2007.
Yang, X., et al., "Higher expression of Caveolin-1 inhibits human small cell cancer (SCLC) apoptosis in vitro", Cancer Invest, vol. 30, pp. 453-462, 2012.
Zeisberg, E.M., et al., "Discovery of endothelial to mesenchymal transition as a source for carcinoma-associated fibroblasts", Cancer Research, vol. 67, pp. 10123-10128, 2007.
Zhang M., et al., "Deletion of caveolin-1 protects hyperoxia-induced apoptosis via survivin-mediated pathways", American Journal of Physiology Lung Cellular and Molecular Physiology, vol. 297, pp. L945-L953, 2009.
Zhang M., et al., "Caveolin-1 mediates Fas-BID signaling in hyperoxia-induced apoptosis", Free Radical Biology & Medicine, vol. 50, No. 10, pp. 1252-1262, 2011.
Zhong, L., et al., "Autoantibodies as potential biomarkers for breast cancer", Breast Cancer Research, vol. 10, pp. 1-8.

Ho, C.C., et al., "Caveolin-1 expression is significantly associated with drug resistance and poor prognosis in advanced non-small cell lung cancer patients treated with gemcitabine-based chemotherapy", Lung Cancer, vol. 59, pp. 105-110, 2008.
Hulit, Jet al., "The cycline D1 gene is transcriptionally repressed by caveolin-1", The Journal of Biological Chemistry, vol. 275, No. 28, pp. 21203-21209, 2000.
Huse, J.T., et al., "Targeting brain cancer: advances in the molecular pathology of malignant glioma and medulloblastoma", Nat Rev Cancer, vol. 10, pp. 319-331, 2010.
International Breast Cancer Study Group, "Toremifene and tamoxifen are equally effective for early-stage breast cancer: first results of International Breast Cancer Study Group Trials 12-93 and 14-93", Annals of Oncology, vol. 15, vol. 12, pp. 1749-1759, 2004.
International Search Report issued in International Application No. PCT/US2010/024606 dated May 4, 2010.
International Search Report issued in International Application No. PCT/US2011/048467 dated Dec. 22, 2011.
International Search Report issued in International Application No. PCT/US2012/022933 dated May 2, 2012.
International Search Report issued in International Application No. PCT/US2013/023209 dated Apr. 9, 2013.
International Search Report issued in International Application No. PCT/US2013/059679 dated Mar. 4, 2014.
International Search Report issued in International Application No. PCT/US2014/034639 dated Aug. 26, 2014.
Iqbal, M., et al., "Potent Inhibitors of Proteasome", J. Med. Chem., vol. 38, No. 13, pp. 2276-2277, 1995.
Jodoin, J., et al., "P-glycoprotein in blood-brain barrier endothelial cells: interaction and oligomerization with caveolins", Journal of Neurochemistry, vol. 87, pp. 1010-1023, 2003.
Jordan, V.C., "A current view of tamoxifen for the treatment and prevention of breast cancer", British Journal of Pharmacology, vol. 110, No. 2, pp. 507-517, 1993.
Joseph, P., et al., "Oncogenic potential of mouse translation elongation factor-1 delta, a novel cadmium-responsive proto-oncogene", J Biol Chem, vol. 277, pp. 6131-6136, 2002.
Kawase, A., et al., "Podoplanin expression by cancer associated fibroblasts predicts poor prognosis of lung adenocarcinoma", Int. J. Cancer, vol. 123, pp. 1053-1059, 2008.
Kay, R.A., et al., "The expression of migration stimulating factor, a potent oncofetal cytokine, is uniquely controlled by 3'-untranslated region-dependent nuclear sequestration of its precursor messenger RNA", Cancer Res, vol. 65, pp. 10742-10749, 2005.
Keown, W.A., et al., "Methods for Introducing DNA into mammalian cells", Methods in Enzymology, vol. 185, pp. 527-537, 1990.
Kerbel, R., et al., "Clinical translation of angiogenesis inhibitors", Nature Reviews, vol. 2, pp. 727-739, 2002.
Kim, H.N., et al., "Caveolin-1 inhibits membrane-type 1 matrix metalloproteinase activity", BMB Reports, vol. 41, pp. 858-862, 2008.
Kim, S., et al., "Basal and UV-induced MMP-1 expression are inhibited by p53 in human dermal fibroblasts", Experimental Dermatology, vol. 17, pp. 939-945, 2008.
Kita, D., et al., "PIK3CA alterations in primary (de novo) and secondary glioblastomas", Acta Neuropathologica, vol. 113, pp. 295-302, 2007.
Koguchi, Y., et al., "TMC-95A, B, C, and D, Novel Proteasome Inhibitors Produced by Apiospora montagnei Sacc. TC 1093 Taxonomy, Production, Isolation, and Biological Activities", The Journal of Antibiotics (Tokyo), vol. 53, No. 2, pp. 105-109, 2000.
Kojima, Y., et al., "Autocrine TGF-beta and stromal cell-derived factor-1 (SDF-1) signaling drives the evolution of tumor-promoting mammary stromal myofibroblasts", Proc Natl Acad Sci USA, vol. 107, pp. 20009-20014, 2010.
Kroll, M., "The secondary fungal metabolite gliotoxin targets proteolytic activities of the proteasome", Chemistry & Biology, vol. 6, No. 10, pp. 689-698, 1999.
Lee, J., et al., "Pyruvate kinase isozyme type M2 (PKM2) interacts and cooperates with Oct-4 in regulating transcription", Int J Biochem Cell Biol, vol. 40, No. 5, pp. 1043-1054, 2008.

(56) References Cited

OTHER PUBLICATIONS

Lei, Y., et al., "Blocking the translation elongation factor-1δ with its antisense mRNA results in a significant reversal of is oncogenic potential", Teratogenesis, Carcinogenesis, and Mutagenesis, vol. 22, No. 5, pp. 377-383, 2002.

Levy, L., et al., "Alterations in components of the TGF-beta superfamily signaling pathways in human cancer", Cytokine Growth Factor Rev, vol. 17, pp. 41-58, 2006.

Lin, M.I., et al., "Caveolin-1-deficient mice have increased tumor microvascular permeability, angiogenesis, and growth", Cancer Res, vol. 67, pp. 2849-2856, 2007.

Lohr, M., et al., "Transforming growth factor-beta1 induces desmoplasia in an experimental model of human pancreatic carcinoma", Cancer Res, vol. 61, pp. 550-555, 2001.

Lopez-Gines, C. et al., "The activation of ERK1/2 MAP kinases in glioblastoma pathobiology and its relationship with EGFR amplification". Neuropathology: Official Journal of the Japanese Society of Neuropathology, vol. 28, No. 5, pp. 507-515, 2008.

Louis, D.N., "Molecular pathology of malignant gliomas", Annu Rev Pathol, vol. 1, pp. 97-117, 2006.

Marastoni M., et al., "Peptidyl Vinyl Ester Derivatives: New Class of Selective Inhibitors of Proteasome Trypsin-Like Activity", Journal of Medicinal Chemistry, vol. 48, No. 15, pp. 5038-5042, 2005.

Martin, S., et al., "Caveolin-1 regulates glioblastoma aggressiveness through the control of alpha(5)beta(1) integrin expression and modulates glioblastoma responsiveness to SJ749, an alpha(5)beta(1) integrin antagonist", Biochim Biophys Acta, vol. 1793, Issue 2, pp. 354-367, 2009.

Martinez-Outschoorn, U.E., et al., "Mitochondrial biogenesis drives tumor cell proliferation", Am J Pathol, vol. 178, pp. 1949-1952, 2011.

Massague, J., "TGFbeta in Cancer", Cell, vol. 134, pp. 215-230, 2008.

Massague, J., "TGF-beta signaling in development and disease", FEBS Lett, vol. 586, p. 1833, 2012.

Meng, L., et al., "Epoxomicin, a potent and selective proteasome inhibitor, exhibits in vivo antiinflammatory activity", Proc. Natl. Acad. Sci., vol. 96, No. 18, pp. 10403-10408, 1999.

Meng, L., et al., "Eponemycin Exerts Its Antitumor Effect through the Inhibition of Proteasome Function", Cancer Research, vol. 59, pp. 2798-2801, 1999.

Mercier, I., et al., "Human breast cancer-associated fibroblasts (CAFs) show caveolin-1 downregulation and RB tumor suppressor functional inactivation", Cancer Biology & Therapy, vol. 7, No. 8, pp. 1212-1225, 2008.

Mercier, I., et al., "Caveolin-1 and accelerated host aging in the breast tumor microenvironment: chemoprevention with rapamycin, an mTOR inhibitor and anti-aging drug", Am J Pathol, vol. 181, pp. 278-293, 2012.

Migita, T., et al., "ATP Citrate Lyase: 1-20 Activation and Therapeutic Implications in Non-Small Cell Lung Cancer", Cancer Research, vol. 68, No. 20, pp. 8547-8554, Oct. 15, 2008.

Millis, R.R., et al., "Immunohistochemical evaluation of biological markers in mammary carcinoma in situ: correlation with morphological features and recently proposed schemes for histological classification", The Breast, vol. 5, No. 3, pp. 113-122, 1996.

Mishra, P.J., et al., "Carcinoma-associated fibroblast-like differentiation of human mesenchymal stem cells", Cancer Res, vol. 68, pp. 4331-4339, 2008.

Mizoguchi, M., et al. "Activation of STAT3, MAPK, and AKT in malignant astrocytic gliomas: correlation with EGFR status, tumor grade, and survival", J Neuropathol Exp Neurol, vol. 65, pp. 1181-1188, 2006.

Monypenny, J., et al., "Cdc42 and Rac family GTPases regulate mode and speed but not direction of primary fibroblast migration during platelet-derived growth factor-dependent chemotaxis", Mol Cell Biol, vol. 29, pp. 2730-2747, 2009.

Nakatani, K., et al., "Expression of caveolin-1 and its correlation with cisplatin sensitivity in oral squamous cell carcinoma", Journal of Cancer Research and Clinical Oncology, vol. 131, pp. 445-452, 2005.

Nam, S., "Ester Bond-containing Tea Polyphenols Potently Inhibit Proteasome Activity in Vitro and in Vivo", The Journal of Biological Chemistry, vol. 276, pp. 13322-13330, 2001.

Navarro, A., et al., "A role for caveolae in cell migration", FASEB J, vol. 18, pp. 1801-1811, 2004.

Nowak, G., et al., "Autocrine production and TGF-beta 1-mediated effects on metabolism and viability in renal cells", Am J Physiol, vol. 271, pp. F689-F697, 1996.

Ohgaki, H., et al., "Genetic pathways to primary and secondary glioblastoma", Am J Pathol, vol. 170, No. 5, pp. 1445-1453, 2007.

Belanger, M.M., et al., "Up-regulation of caveolin expression cytotoxic agents in drug-sensitive cancer cells", Anti-Cancer Drugs, vol. 14, No. 4, pp. 281-287, 2003.

Herzog, M., et al., "Knockdown of caveolin-1 decreases activity of breast cancer resistance protein (BCRP/ABCG2) and increases chemotherapeutic sensitivity", Naunyn-Schmied Arch Pharmacol, vol. 383, pp. 1-11, 2011.

Ho, Chao-Chi, et al., "Caveolin-1 expression is significantly associated with drug resistance and poor progosis in advanced non-small cell lung cancer patients treated with gemcitabine-based chemotherapy", Lung Cancer, vol. 59, pp. 105-110, 2008.

Lavie, Y., et al., "Up-regulation of Caveolae Caveolkar Constituents in Multidrug-resistant Cancer Cells", The Journal of Biological Chemistry, vol. 273, No. 49, pp. 32380-32383, 1998.

Senetta, R., et al., "Caveolin 1 Expression Independently Predicts Shorter Survival in Oligodendrogliomas", J Neuropathol Exp Neurol, vol. 68, No. 4, pp. 425-431, 2009.

Senetta, R., et al., "Epidermal growth factor receptor and caveolin-1 coexpression identifies adult supratentorial ependymomas with rapid unfavorable outcomes", Neuro-Oncology, vol. 13, No. 2, pp. 176-183, 2011.

Thompson, T.C., et al., "Caveolin-1, a metastasis-related gene that promotes cell survival in prostate cancer", Apoptosis, vol. 4, No. 4, pp. 233-237, 1999.

Yang, C.-P.H., et al., "Upregulation of caveolin-1 and caveolae organelles in Taxol-resistant A549 cells", FEBS Letters, vol. 439, pp. 368-372, 1998.

Yoo, Seong-Ho, et al., Expression of caveolin-1 is associated with poor prognosis of patients with squamous cell arcinoma of the lung, Lung Cancer, vol. 42, pp. 19-202, 2003.

* cited by examiner

MCT PROTEIN INHIBITOR-RELATED PROGNOSTIC AND THERAPEUTIC METHODS

CROSS-REFERENCE TO RELATED APPLICATIONS

This application is a U.S. National Phase Application under 35 U.S.C. 371 of International Application No. PCT/US13/23209, filed Jan. 25, 2013, which claims priority of U.S. Provisional Application No. 61/591,473, filed Jan. 27, 2012, the contents of all of which are incorporated herein by reference.

BACKGROUND OF THE INVENTION

Previously, we identified a loss of stromal Cav-1 as a predictive biomarker of early tumor recurrence, metastasis, tamoxifen-resistance, and decreased survival in human breast cancer patients[1,2]. The predictive value of a loss of stromal Cav-1 was independent of epithelial marker status, as a loss of stromal Cav-1 was predictive in ER+, PR+, HER2+, and triple-negative breast cancer patients[1,2]. Similarly, in DCIS-patients, a loss of stromal Cav-1 in breast cancers has now been independently validated by six other groups world-wide (Australia, Argentina, Korea, Japan, Egypt, and Leeds-UK)[4-8], and has been extended to other types of human cancers, such as advanced prostate cancer[9], and metastic melanoma[10].

To mechanistically understand the prognostic basis of a loss of stromal Cav-1, we studied Cav-1-deficient-mice. Metabolomic, proteomic, and genomic profiling established that fibroblasts and the mammary fad pads from Cav-1-deficient mice are highly-catabolic, and show strong meta-bolic-shifts towards autophagy/mitophagy, and aerobic glycolysis, due to increased oxidative stress[11-15]. Virtually identical catabolic processes and associations with aerobic glycolysis were identified via analysis of laser-captured tumor stroma from human breast cancer patients lacking stromal Cav-1[16]. This led to the proposal of a novel two-compartment model of tumor metabolism, termed the "Reverse Warburg Effect"[11, 17-24]. In this model, the glycolytic tumor stroma transfers energy-rich nutrients (such as, L-lactate and ketone bodies) to anabolic tumor cells, which then "fuels" mitochondrial metabolism in epithelial cancer cells[18].

Thus, we searched for new biomarker(s) of clinical outcome, by analyzing breast cancer cells co-cultured with human fibroblasts. In this co-culture system, Cav-1 is degraded by oxidative-stress-induced autophagy in cancer-associated fibroblasts, resulting in a loss of stromal Cav-1 expression[25-28], mirroring what we observe in high-risk breast cancer patients. Under the same conditions, we demonstrated that breast cancer cells induce MCT4 over-expression in stromal fibroblasts, and that MCT4-induction can be prevented by anti-oxidants[29]. Importantly, MCT4 is the major transporter directly responsible for L-lactate efflux/export from glycolytic cells. As such, MCT4 is a functional biological marker of oxidative stress (pseudo-hypoxia) and aerobic glycolysis in the tumor stroma[29].

However, it remains unknown if MCT4 levels are controlled by Cav-1 and/or if stromal MCT4 has any prognostic value as a biomarker in breast cancer patients. To address this issue, we evaluated the prognostic value of stromal Cav-1 and stromal MCT4, in parallel, in the same triple-negative breast cancer patient cohort.

Here, we show that stromal MCT4 (i) is a new biomarker that independently predicts poor overall survival in triple negative (TN) breast cancer patients, and (ii) stromal MCT4 can be used in conjunction with stromal Cav-1, to further stratify the intermediate-risk group into high-risk and low-risk patients.

As MCT4 is a new druggable-target, we suggest that MCT4 inhibitors should be developed for the treatment of aggressive breast cancers, and possibly other types of human cancers.

SUMMARY OF THE INVENTION

This invention provides a method of identifying one or more subgroups of cancer patients that are likely to benefit from treatment with a monocarboxylate transporter (MCT) protein inhibitor or not likely to benefit from treatment with said MCT protein inhibitor, comprising: (a) obtaining a sample of a cancer/tumor tissue from each of said cancer patients; (b) determining the expression level of stromal MCT4 protein in each of said samples of cancer/tumor tissue to obtain a first dataset; and (c) using the expression level of the stromal MCT4 protein from said first dataset to classify each of said sets of one or more cancer patients as stromal MCT4-positive or stromal MCT4-negative, wherein the cancer patients classified as stromal MCT4-positive are patients that are more likely to benefit from treatment with said MCT protein inhibitor, and wherein the patients classified as stromal MCT4-negative are not likely to benefit from treatment with an MCT protein inhibitor.

This invention also provides a A method for treating a cancer/tumor whose stromal component expresses the MCT4 protein in a patient, comprising: (a) obtaining a sample of a cancer/tumor tissue from said patient; (b) determining the expression level of stromal MCT4 protein in said sample of cancer/tumor tissue; and (c) if said stromal component of said cancer is determined to express MCT4 protein, administering to said patient an MCT protein inhibitor.

This invention further provides a method for prognostic assessment of cancer in a subject, the method comprising (a) providing a biological sample from a cancer/tumor tissue derived from said subject; and (b) determining the level of MCT4 protein in the stromal component of said cancer/tumor tissue, wherein if said stromal component of said cancer tumor tissue is determined to express MCT4 protein, then a poor prognosis of said cancer is indicated/predicted.

This invention further provides a method for determining if a cancer/tumor patient is likely to benefit from treatment with a monocarboxylate transporter (MCT) protein inhibitor, comprising (a) determining the expression level of stromal MCT4 protein in a sample of the patient's cancer/tumor tissue; and (b) classifying the patient as stromal MCT4-positive or stromal MCT4-negative, wherein the patient classified as stromal MCT4-positive is likely to benefit from treatment with the MCT protein inhibitor, and the patient classified as stromal MCT4-negative is not likely to benefit from treatment with the MCT protein inhibitor.

Finally, this invention provides a method for treating a patient afflicted with a cancer/tumor whose stromal component is MCT4-positive, comprising administering to the patient a therapeutically effective amount of an MCT protein inhibitor.

Figure 2:
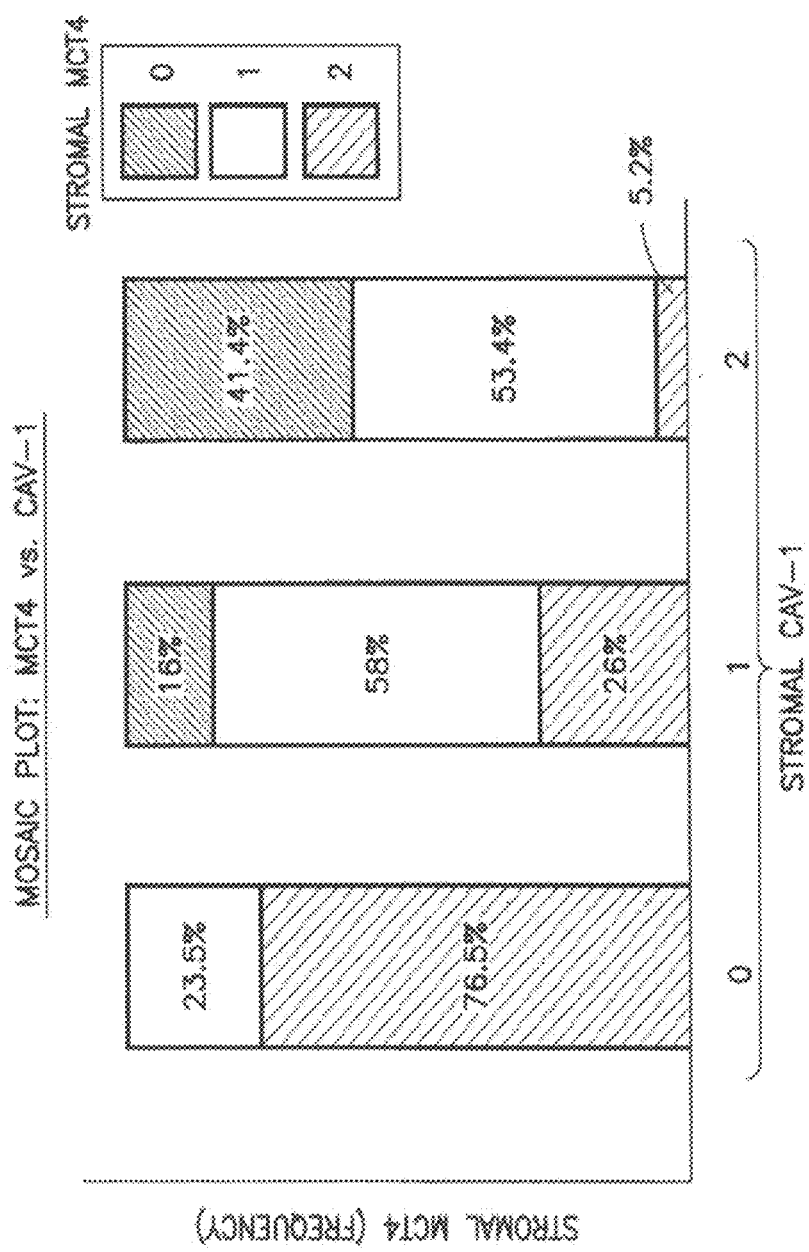

FIG. 2. The Levels of Stromal MCT4 and Stromal Cav-1 are Inversely Related in Human Breast Cancer. A mosaic plot of the joint distribution of stromal Cav-1 and stromal MCT4 is shown. Note that there is clearly a negative relationship between the two biomarkers. For example, if stromal Cav-1=0, you are mostly likely observe stromal MCT4=2. Conversely, if stromal Cav-1=2, you are most likely to observe stromal MCT4=0 or 1. For specific numbers, see Table 2.

Figure 3:
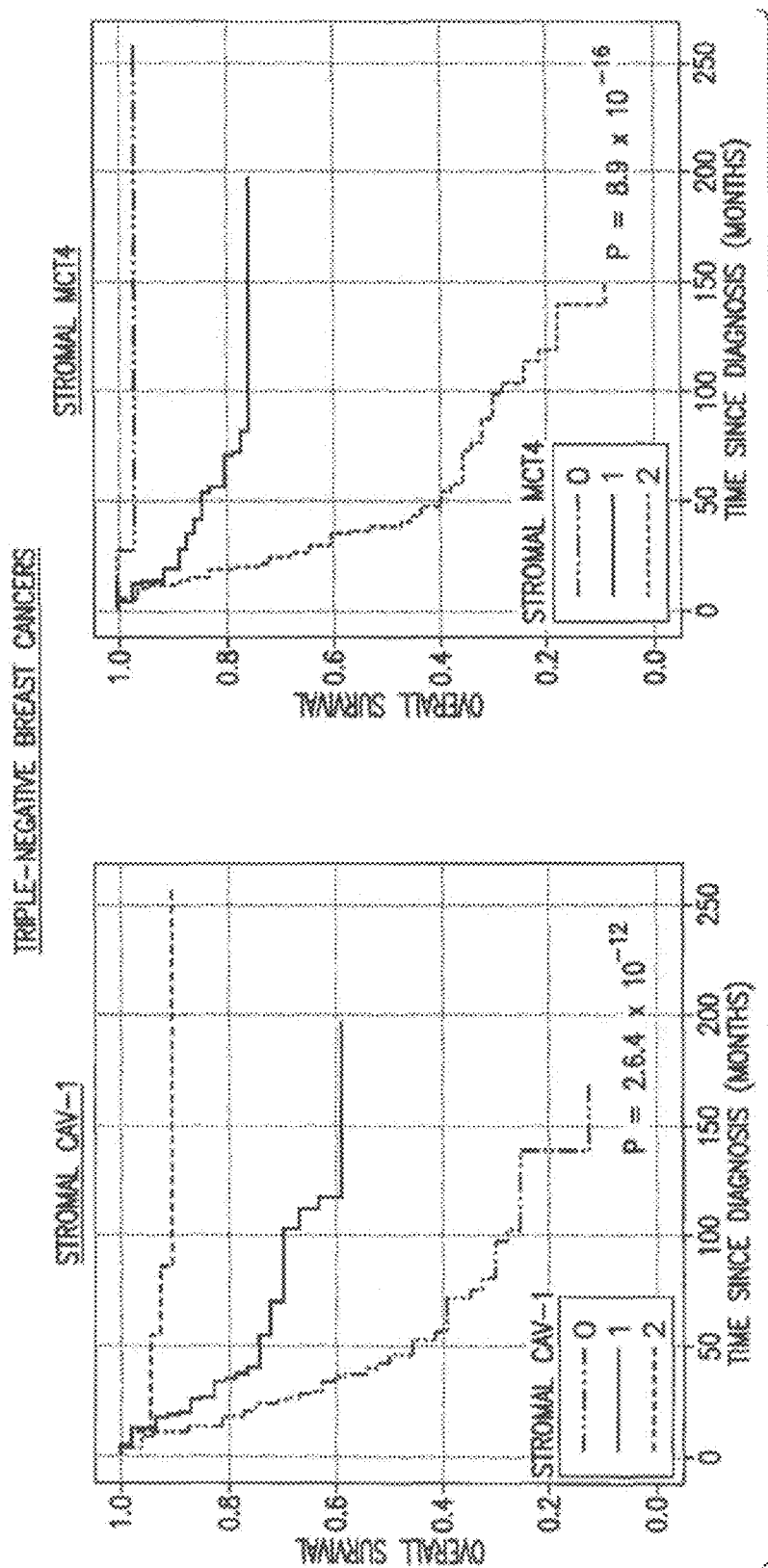

FIG. 3. Kalplan-Meier Analysis Reveals the Prognostic Value of Stromal MCT4: Comparison with Stromal Cav-1. Stromal Cav-1 and stromal MCT4 levels were used to generate Kaplan-Meier survival curves, plotting percent overall survival (%) versus time since diagnosis (in months). The results of this analysis were highly statistically significant (with p-values in the range of $10^{12}$ to $10^{16}$). This analysis identified the two high-risk groups as patients with absent stromal Cav-1 (score 0; N 51 patients) and high stromal MCT4 (score −2; N=(5 patients).

Figure 4:
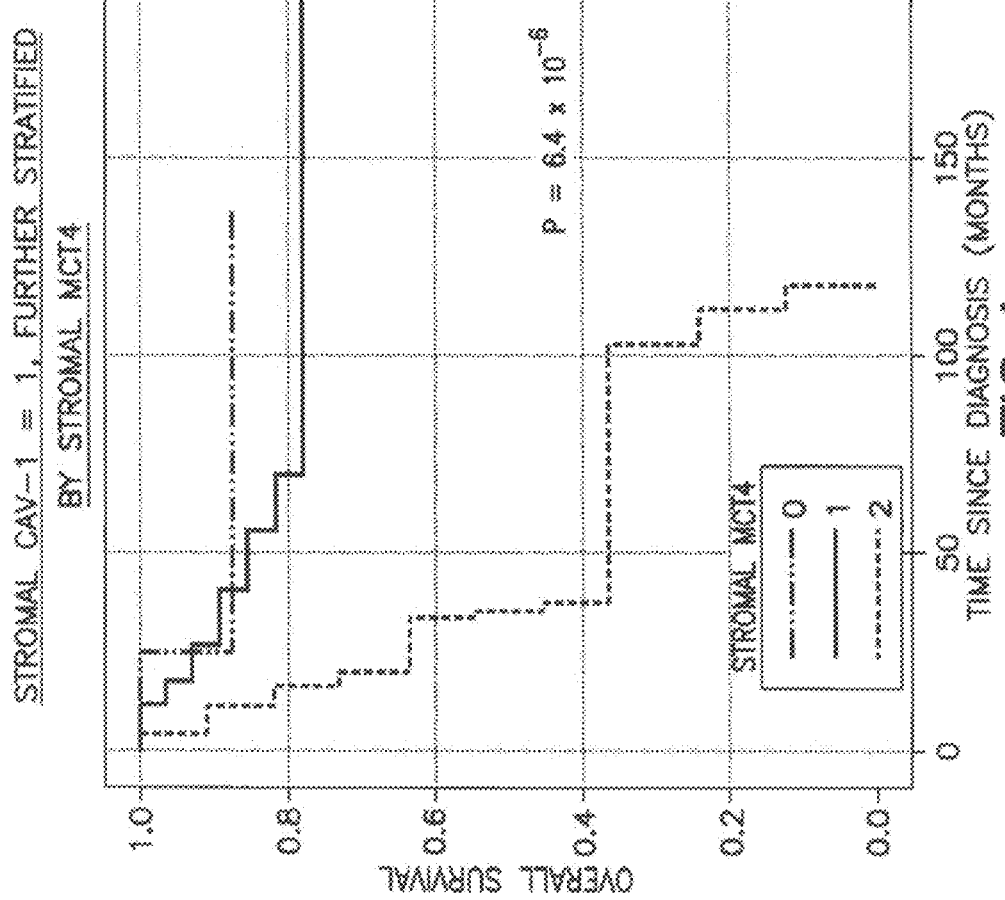

FIG. 4. Combined Use of Stromal Cav-1 and Stromal MCT4 for Stratification of the Intermediate Risk Group (Stromal Cav-1=1). The intermediate risk group identified by stromal Cav-1 (score 1) could be further stratified using stromal MCT4, allowing the unambiguous identification of high-risk and low-risk patients. More specifically, patients with stromal Cav-1 (score 1) could be further divided into high- and low-risk groups using stromal MCT4, yielding 10-year survival rates of ~78-88% versus <1% survival.

Figure 5:
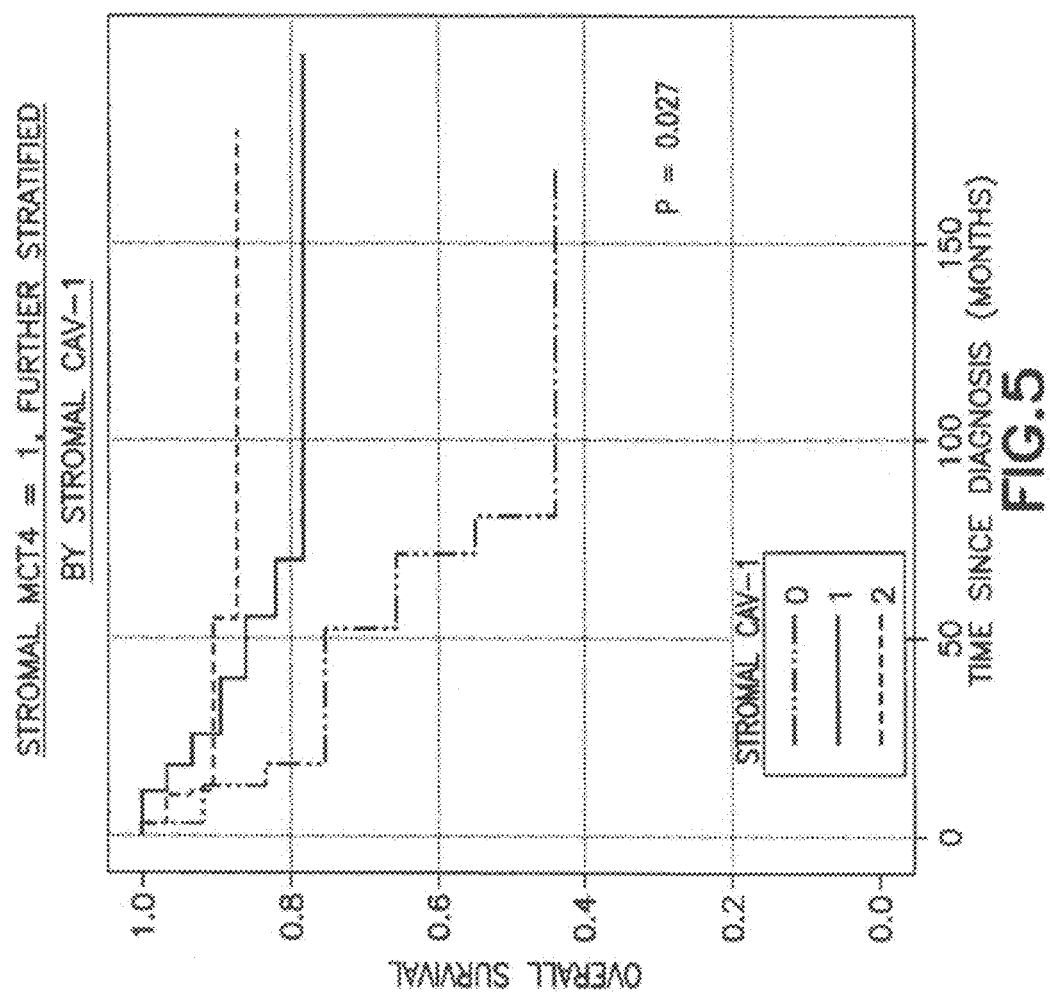

FIG. 5. Combined Use of Stroma MCT4 and Stromal Cav-1 for Stratification of the Intermediate Risk Group (Stromal MCT4=1). The intermediate risk group identified by stromal MCT4 (score 1) could be further stratified using stromal Cav-1, allowing the unambiguous identification of high-risk and low-risk patients. More specifically, patients with stromal MCT4 (score=1) could be further divided into high- and low-risk groups using stromal Cav-1, yielding 10-year survival rates of −78-87% versus <45% survival.

Figure 6:
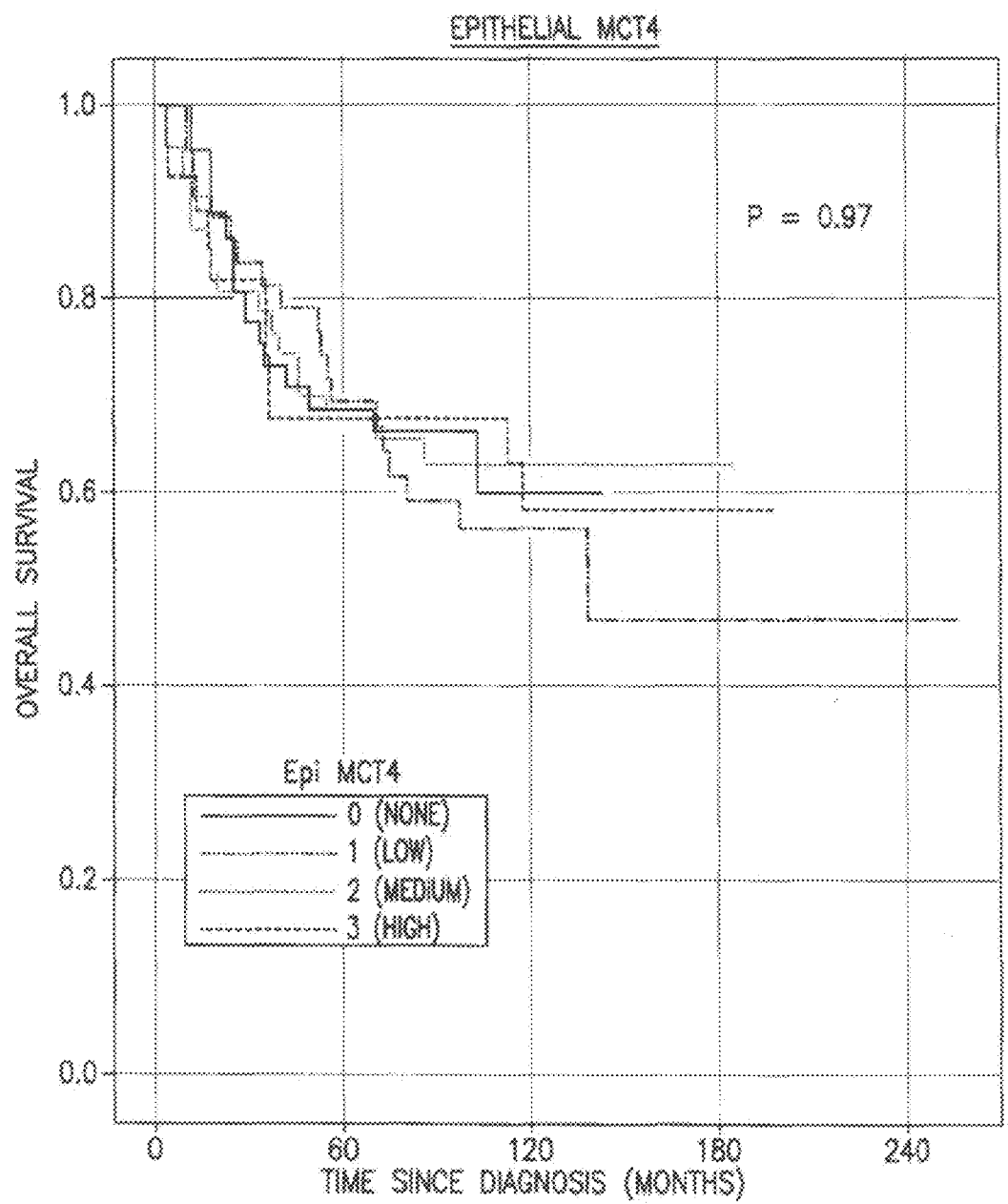

FIG. 6. MCT4 Levels in Tumor Epithelial Cells have No Prognostic Value. In a parallel analysis carried out on the same patient TMAs, the levels of tumor epithelial MCT4 were scored. However, they showed no prognostic significance (P=0.97). Thus, the prognostic value of MCT4 expression is restricted to the tumor stroma.

Figure 7:
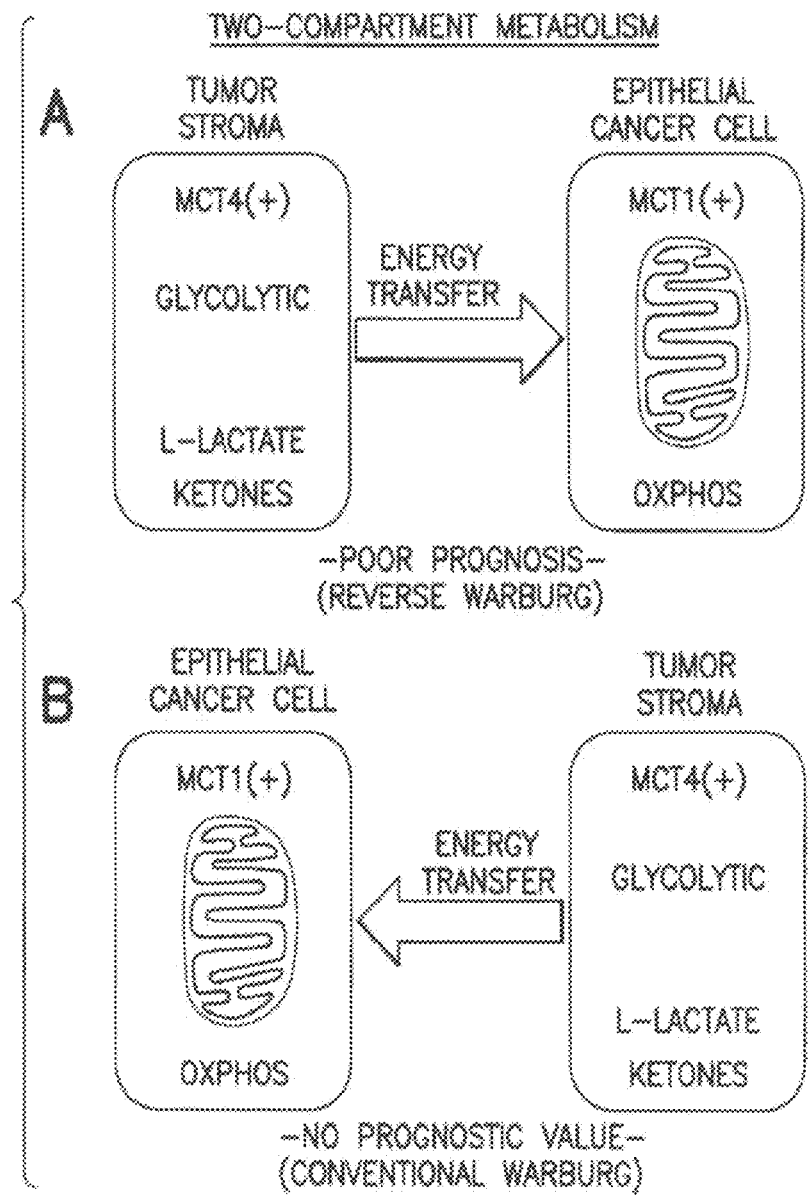

FIG. 7. Two-Compartment Tumor Metabolism MCT4 Expression and the Warburg Effect. Here, we directly compared the prognostic value of stromal and epithelial MCT4 expression in triple-negative breast cancer patients, within the same patient cohort. MCT4 expression is a specific marker of aerobic glycolysis (with enhanced L-lactate and ketone production), also known as the Warburg effect. Our results directly show that high stromal MCT4 levels are specifically associated with poor overall survival (panel A). In contrast, expression of MCT4 in epithelial tumor cells had no prognostic value (panel B). Thus, only induction of the Warburg effect in the tumor stroma has prognostic value. In both panels A and B, note that glycolytic MCT4(+) cells would be metabolically coupled with oxidative mitochondria metabolism (OXPHOS) in adjacent MCT1(+) cells, resulting net energy transfer (REI arrows). MCT4 normally functions in L-lactate efflux/export, while MCT1 functions in L-lactate uptake/import.

Figure 8:
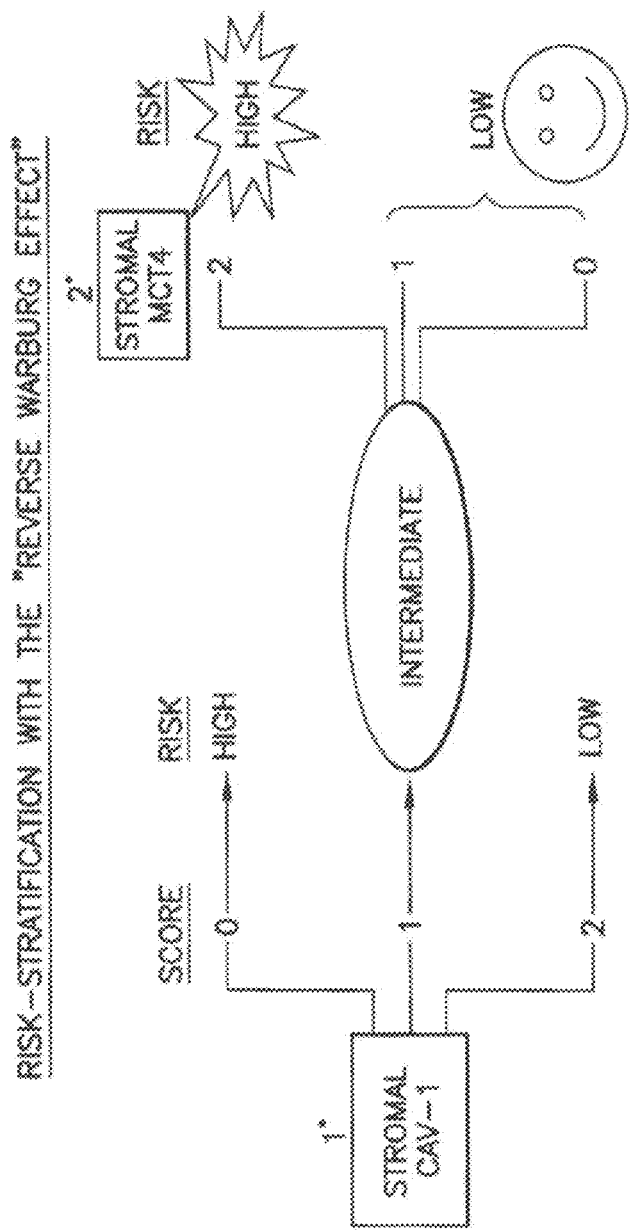

FIG. 8. Combining: Stromal Cav-1 with Stromal MCT4 Allows for More Powerful Prognostic Stratification. Based on our current studies, patients would first be stratified into high-, intermediate- and low-risk groups, based on the levels of stromal Cav-1 (as a primary biomarker). Then, patients in the intermediate-risk group (with stromal Cav-1=1) could be further stratified into high- and low-risk groups, using stromal MCT4 (as a secondary biomarker). High-risk patients, with stromal MCT4=2, could be treated differently than lower-risk patients, with stromal MCT4=0 and 1, allowing for more personalized cancer care.

DETAILED DESCRIPTION OF THE INVENTION

We have recently proposed a new model of cancer metabolism to explain the role of aerobic glycolysis and L-lactate production in fueling tumor growth and metastasis. In this model, cancer cells secrete hydrogen peroxide (H202), initiating oxidative stress and aerobic glycolysis in the tumor stroma. This, in turn, drives L-lactate secretion from cancer-associated fibroblasts. Secreted L-lactate then fuels oxidative mitochondrial metabolism (OXPHOS) in epithelial cancer cells, by acting as a paracrine oncometabolite. We have previously termed this type of two-compartment tumor metabolism the "Reverse Warburg Effect", as aerobic glycolysis takes place in stromal fibroblasts, rather than epithelial cancer cells. In this invention, we used MCT4 immuno-staining of human breast cancer tissue microarrays (TMAs; >180 triple-negative patients) to directly assess the prognostic value of the "Reverse Warburg Effect". MCT4 expression is a functional marker of hypoxia, oxidative stress, aerobic glycolysis, and L-lactate efflux. Remarkably, high stromal MCT4 levels (score=2) were specifically associated with decreased overall survival (<18°/survival at 10-years post-diagnosis). In contrast, patients with absent stromal MCT4 expression (score=0), had 10-year survival rates of −97% (p-value $<10^{-32}$). High stromal levels of MCT4 were strictly correlated with a loss of stromal Cav-1 (p-value $<10^{-14}$), a known marker of early tumor recurrence and metastasis. In fact, the combined use of stromal Cav-1 and stromal MCT4 allowed us to more precisely identify high-risk triple-negative breast cancer patients, consistent with the goal of individualized risk-assessment and personalized cancer treatment. However, epithelial MCT4 staining had no prognostic value, indicating that the "conventional" Warburg effect does not predict clinical outcome. Thus, the "Reverse Warburg Effect" or "parasitic" energy-transfer is a key determinant of poor overall patient survival. As MCT4 is a druggable-target, MCT4 inhibitors should be developed for the treatment of aggressive breast cancers, and possibly other types of human cancers. Similarly, we discuss how stromal MCT4 could be used as a biomarker for identifying high-risk cancer patients that could likely benefit from treatment with FDA-approved drugs or existing MCT-inhibitors (such as, AR-C1558 8, AR-C117977, and AZD-3965).

EXPERIMENTAL DETAILS

Materials and Methods

Materials.
Anti-MCT4 isoform-specific rabbit polyclonal antibodies were previously generated and characterized by Dr. Nancy Philp[30]. Isoform-specific antibodies were produced against the 18-mer synthetic oligopeptide corresponding to the carboxyl terminal amino acids of MCT4[30].

The Study Population and Tumor Microarray Construction.

Cases for the study where obtained from the Surgical Pathology files at the Thomas Jefferson University, with Institutional Review Board approval. The tissue-microarray (TMA) contained tumor samples derived from 181 largely consecutive patients with triple negative breast carcinoma (with follow-up information) treated at the Thomas Jefferson University. For inclusion in this study as TN breast cancer, expression of estrogen, progesterone receptors was not detected or present in <1% of tumor cells, with a satisfactory positive control. HER2 was scored 0-1+ or 2+, and an absence of HER2 amplification by fluorescent in situ hybridization was required for negativity. All cases were invasive ductal carcinomas (IDC). Clinical and pathological variables were determined following well-established criteria. All TN breast cancers were graded according to the method described by Elston and Ellis; lymphovascular invasion was classified as either present or absent. The tumor tissue-microarrays (TMAs) were constructed using a tissue arrayer (Veridiam, San Diego, Calif.). Two tissue cores (0.6 μm diameter) were sampled from each block to account for tumor and tissue heterogeneity and transferred to the recipient block. Clinical and treatment information as extracted by chart review.

Immunostaining.

Cav-1 and MCT4 expression levels were assessed using a standard 3-step avidin-biotin immunoperoxide method, with a rabbit polyclonal anti-Cav-1 antibody (Santa Cruz Biotech, Inc. (N-20; sc-894, Santa Cruz Biotech, diluted 1:1,000) or a rabbit polyclonal anti-MCT4 antibody (diluted 1:250) a 3-step avidin biotin immunoperoxidase method. TMA sections were de-paraffinized and re-hydrated through graded alcohols. Antigen retrievals as performed in 10 mM citrate buffer, pH 6.0 for 10 min in a pressure cooker. Sections were cooled to room temperature, rinsed in PBS, blocked with 3% (v/v) $H_2O_2$ for 15 min, followed by blocking for endogenous biotin using the DakoCytomation Biotin Blocking System cat#X0590. Slides were then incubated for 1 hour with 10% goat serum and incubated with primary antibody overnight at 4° C. Antibody binding was detected using a biotinylated secondary antibody (Vector Labs, cat#BA-1000) followed by streptavidin-HRP (Dako cat#K 1016). Immunoreactivity was detected using Dako Liquid DAB+Substrate-Chromogen Solution.

Stromal Scoring.

Stromal Cav-1 staining was scored semi-quantitatively as negative (0, no staining), weak (1, either diffuse weak staining or strong staining in less than 30% of stromal cells per core), or strong 2, defined as strong staining of 30% or more of the stromal cells)[1-3]. MCT4 expression in the stroma was performed using same criteria as those we applied for scoring Cav-1 expression.

Epithelial Scoring.

For evaluating MCT4 expression in tumor epithelial cells, we used a previously developed scoring system[31]. Sections were scored semi-quantitatively as follows: 0, 0% immuno-reactive cells; 1, <5% immuno-reactive cells; 2, 5-50% immuno reactive cells; and 3, >50% reactive cells. Similarly, intensity of staining was evaluated semi-quantitatively on a scale 0-3 with 0, representing negative, 1, weak, 2, moderate and 3, strong staining. Then the final score was calculated, reflecting both the percent of immuno-reactive cells and staining intensity.

Statistical Analysis.

As noted, we scored stromal Cav-1 and MCT4 expression in the TMAs as 0 (none), 1 (low) and 2 (high). Epithelial MCT4 was scored as 0 (none), 1 (low), 2 (medium) and 3 (high). The outcome of interest here is overall survival, i.e. death can occur for any cause. Survival curves were computed by expression strata using the Kaplan-Meier method, and differences between survival curves was assessed using the log-rank test. Hazard ratios for the biomarkers were computed using Cox proportional hazards regression, using the biomarker as predictor and adjusting for age and race. Agreement with the proportional hazards assumption was verified. Differences in 10-year survival were assessed based on two-sample z-tests, using estimates and standard errors from the Kaplan-Meier curves. All analyses were done using the statistical analysis package R version 2.13[32], along with the R package survival version 2.36-9[33]. Associations were assessed using the χ-test for independence.

Results

Predicting Overall Survival in Triple-Negative (TN) Breast Cancer Patients: Assessing the Prognostic Value of Stromal MCT4

Here, we investigated the predictive value of stromal MCT4 as a new candidate biomarker, for determining clinical outcome in TN breast cancer patients. More specifically, we used anti-MCT4 isoform-specific polyclonal antibodies to immuno-stain a tumor tissue microarray (TMA) containing paraffin-sections taken from TN breast cancer patients at surgical resection. This TMA cohort is well-annotated, and contains 181 patients seen at Thomas Jefferson University Hospital (TJUH), with up to 250 months (>20-years) of follow-up. In this TN breast cancer population, our main outcome of interest was overall survival. For comparison, the expression of MCT4 was scored in both the epithelial and stromal compartments. Also, the same TN-TMA was immune-stained for stromal Cav-1 expression. Table 1 shows the descriptive statistics (age, race, tumor size, histologic grade, stage, and lymph-node status) for the entire patient population.

Stromal MCT4 and Stromal Cav-1 Levels are Inversely Related

Figure 1:
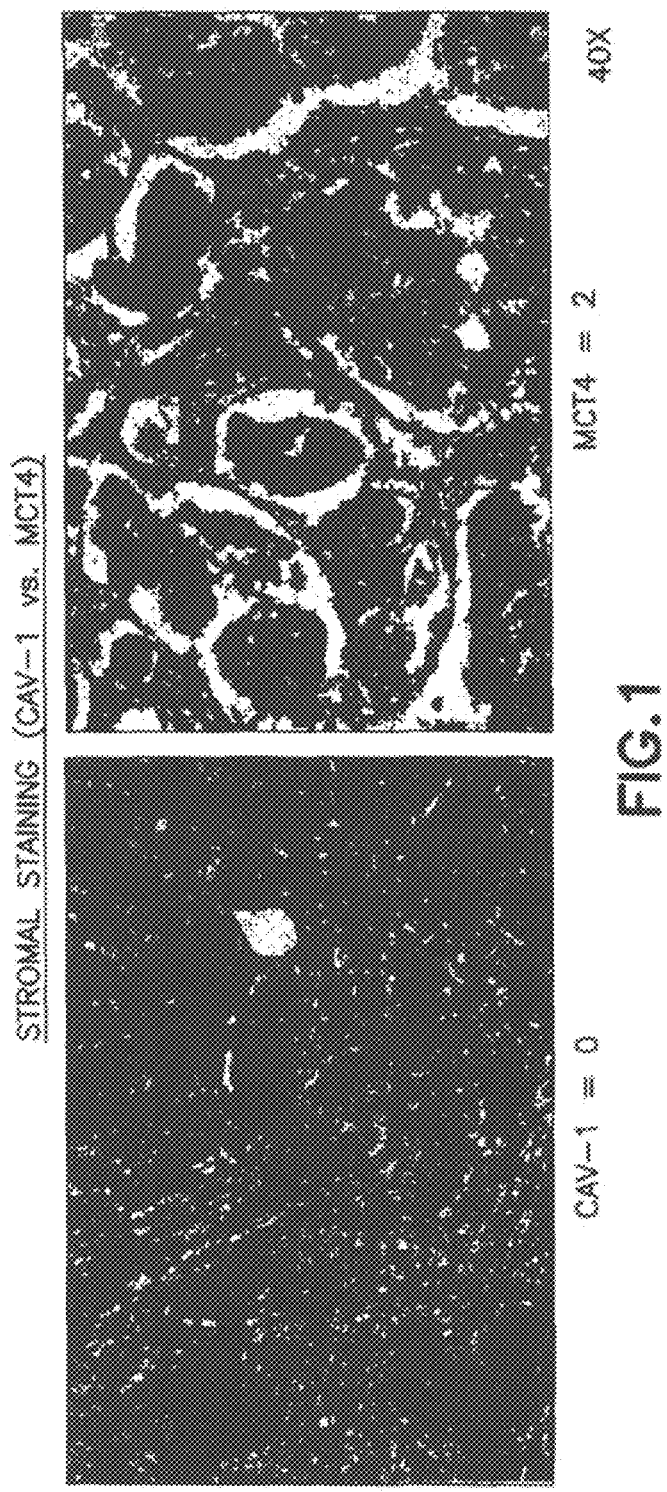
FIG. 1. Cav-1 and MCT4: Stromal Staining in Human Breast Cancer Patients. Note the high expression of MCT4 in the tumor-stroma and cancer-associated fibroblasts in a subset of TN breast cancer patients which is associated with a loss of stromal Cav-1 (Table 2). Representative images or patients in the stromal high-risk groups are shown (Cav-1=0 and MCT4=2). Despite a loss of stromal Cav-1 immuno-staining, blood vessels remain Cav-1-positive, as endothelial cells are resistant to oxidative stress. Original magnification, 40×.

Representative images of MCT4 staining are shown in FIG. 1, highlighting the MCT4 expression in the stromal compartment. Of the 181 TN breast cancer cases examined, 164 could be effectively scored for stromal MCT4 staining (0=no staining; 1=mild-or-moderate staining; 2=strong staining). Similarly, 159 patients could be effectively scored for stromal Cav-1 staining.

Interestingly, the expression levels of stromal MCT4 and stromal Cav-1 were inversely related. High levels of stromal MCT4 directly correlated with a loss of stromal Cav-1 immuno-staining, with a p-value of $5 \times 10^{-15}$. Table 2 shows the joint frequency distribution of stromal MCT4 and stromal Cav-1, and FIG. 2 presents a mosaic-plot of the data.

In this joint frequency distribution analysis, 55 patients showed high levels of MCT4 stromal staining, 72 showed moderate staining, and 32 showed an absence of MCT4 stromal staining.

Similarly, 58 patients showed high levels of Cav-1 stromal staining, 50 showed and intermediate level of staining, and 51 showed an absence of Cav-1 stromal staining.

Most notably, patients with stroma Cav-1=0 are most likely to be stromal MCT4=2. Conversely, patients with stromal Cav-1=2 are most likely to be stromal MCT4=0 or 1. Interestingly, we could not detect any patients with concomitant loss of both stromal Cav-1(Cav-1=0) and stromal MCT4 (MCT4=0), indicating that a loss of stromal Cav-1 is strictly correlated with increased MCT4 expression. Conversely, only very few cases (3 out of 159=2%) had high stromal expression of both MCT4 and Ca-11, indicating that high stromal MCT4 and high stromal Cav-1 are nearly mutually exclusive events.

High Stromal MCT4 Predicts Poor Overall Survival

Stromal Cav-1 and stromal MCT levels were also used to generate Kaplan-Meier survival curves, plotting percent survival (%) versus time since diagnosis (in months) (FIG. 3). The results of this analysis were highly statistically significant (with p-values in the range of $10^{-12}$ to $10^{-16}$).

This univariate analysis identified the two high-risk groups as patients with i) absent stromal Cav-1 (score=0; N=51 patients) and ii) high stromal MCT4 (score=2; N=55 patients). Notably, the intersection of these two high-risk groups shows considerable overlap, with N=39 patients in co on Table 2).

Hazard ratios are shown in Tables 3& 4, with stromal Cav-1 and stromal MCT4 showing 14-fold and 50-fold differences in relative risk stratification, respectively.

In addition, 10-year survival rates are shown in Tables 5& 6. For example, if stromal MCT4=0, the 10-year survival rate was ~97% versus <20% for stromal MCT4=2.

Conversely, if stromal Cav-1=2, the 10-year survival rate was ~91% versus ~25% for stromal Cav-1=0.

Combining Stromal Cav-1 with Stromal MCT4 Allows Further Stratification of the Intermediate Risk Group Notably, the two intermediate risk groups identified by stromal Cav-1 (score-1) and stromal MCT4 (score=1) could be further stratified by combining both stromal markers, allowing the unambiguous identification of high-risk and low-risk patients (FIGS. 4 & 5; and Tables 5 & 6).

For example, patients with stromal Cav-1 (score=1) could be further sub-divided into high- and low-risk groups using stromal MCT4 (FIG. 4 and Table 5). Remarkably, in this intermediate risk group (Cav-1=1), the 10-year survival rates sharply decline from 88% (MCT4=0) and 78% (MCT4=1), to <1% (MCT4=2).

MCT4 Expression in Tumor Epithelial Cells has No Prognostic Value

Finally, in a parallel analysis carried out on the same exact patient TMAs, the levels of tumor epithelial MCT4 were scored (FIG. 6). However, they showed no prognostic significance (P=0.97). Thus, the prognostic value of MCT4 expression is highly compartment-specific, and restricted to the tumor stroma.

Similarly, we have previously shown that tumor epithelial Cav-1 levels have no prognostic value in two different breast cancer cohorts[1,2].

Discussion

Tow-Compartment Tumor Metabolism: the Reverse Warburg Effect

In 1889, Dr. Paget proposed the "Seed and Soil Hypothesis", suggesting that cancer cells (the seeds) require a permissive microenvironment (the soil to facilitate tumor growth, progression and metastatic dissemination[34-36].

Recently, it has been proposed that oxidative stress in the tumor microenvironment may function as "fertilizer", by driving DNA-damage, inflammation, and metabolic alterations[24, 37-39]. Tumor cells secrete hydrogen peroxide (H2O2) to induce oxidative stress (pseudo-hypoxia), "fertilizing" the tumor stroma[28]. As a consequence, oxidative stress initiated by tumor cells in transferred to cancer-associated fibroblasts[28].

Oxidative stress in cancer-associated fibroblasts then result in increased stromal ROS production, and the activation of NFkB and HIF1-alpha transcription factors, inducing autophagy/mitophagy, inflammation, and aerobic glycolysis. Mitophagy (mitochondrial autophagy) then increases L-lactate and ketone production, due to a mitochondrial dysfunction or deficiency[26,27,40].

As a consequence, tumor-associated fibroblasts release high-energy metabolites (L-lactate and ketones) and chemical building blocks (nucleotides, fatty acids, and amino acids, such as glutamine). These catabolites stimulate mitochondrial biogenesis, OXPHOS, and autophagy-resistance in epithelial cancer cells, and protect cancer cells against chemotherapy-induced apoptosis[17, 41, 42].

We have termed this new model of cancer metabolism the "Reverse Warburg Effect", as aerobic glycolysis takes place in stromal fibroblasts, and not in epithelial tumor cells[11, 17, 18] (FIG. 7).

In this two-compartment system, oxidative cancer cells and glycolytic fibroblasts are metabolically-coupled, in a host parasite relationship[17]. Tumor cells directly "feed" off the glycolytic host microenvironment, behaving like an infectious parasite[18]. Thus, two-compartment tumor metabolism may be the basis of chemo-resistance or therapy-failure in cancer patients[17]. We have also demonstrated that ROS produced in cancer-associated fibroblasts, has a "bystander effect" on adjacent epithelial cancer cells, leading to DNA-damage, genomic-instability and aneuploidy[26].

In summary, we believe that a critical biological function of the tumor stroma is to produce L-lactate and other high-energy catabolites (such as ketones and glutamine) to "fuel" oxidative mitochondrial metabolism (OXPHOS) in adjacent epithelial cancer cells[43-47].

MCT4 and Normal Lactate Transport

Specialized transporters, termed monocarboxylate transporters (MCTs), function as "shuttles" to transfer L-lactate from one cell-type to another[48, 49]. For example, MCT4 is primarily a transporter that extrudes L-lactate from cells that utilize aerobic glycolysis for energy metabolism and lack functional mitochondria[50]. Ketones are thought to be transported by the same MCT transporters that handle lactate transport. Physiologically, MCT4 expression is induced by hypoxia and/or oxidative stress, and MCT4 is a known HIF 1-alpha target gene[48,51] Thus, MCT4 is a functional marker of oxidative stress and aerobic glycolysis, also known as the "Warburg Effect"[29].

Two physiological examples of cells that normally undergo the aerobic glycolysis are fast-twitch fibers in skeletal muscle and astrocytes in the brain[52-56]. In skeletal muscle, MCT4 is selectively expressed in fast-twitch fibers that are glycolytic, and extrude lactate, which is then taken up by slow-twitch fibers[48, 49]. In the brain, MCT4 is selectively expressed in astrocytes which are glycolytic, and export lactate, that is used as an energy source by adjacent neurons[48, 49]. In skeletal muscle, such metabolic-coupling is known as the "Lactate Shuttle" and in the brain, it is called "Neuro-Glia Metabolic Coupling"[52-56]. These normal physiologic forms of metabolic-coupling are analogous to the "Reverse Warburg Effect", which is observe in tumor tissue[29].

MCT4 and the Reverse Warburg Effect

Here, we investigated the compartment-specific expression of MCT4 in human breast cancer patients, and determined its potential association with overall clinical outcome. As MCT4 is a marker of oxidative stress and aerobic glycolysis, as well as L-lactate extrusion, it should allow us to determine if the "Warburg Effect" shows any prognostic value, in epithelial cancer cells, or the tumor stroma, or in both tumor compartments.

In the conventional Warburg effect, epithelial cancer cells undergo aerobic glycolysis, likely due to mitochondrial dysfunction[57, 60], and are predicted to express high levels of MCT4. Conversely, in the "Reverse Warburg Effect", stromal fibroblasts undergo aerobic glycolysis, due to oxidative stress, and autophagy/mitophagy in the tumor stroma, resulting in a functional mitochondrial deficiency. As such, in the Reverse Warburg Effect", cancer-associated fibroblasts and the tumor stroma should over-express MCT4[29]. In both scenarios, glycolytic MCT4(+) cells would be metabolically-coupled with oxidative mitochondrial metabolism (OXPHOS) in adjacent MCT1(+) cells: MCT4 functions in L-lactate efflux, while MCT1 functions in L-lactate uptake (FIG. 7).

Thus, we directly compared the prognostic value of stromal and epithelial MCT4 expression in triple-negative breast cancer patients, within the same patient cohort. Our results directly show that high stromal MCT4 levels are specifically associated with poor overall survival. In contrast, expression of MCT4 in epithelial tumor cells had no prognostic value. As a result, it appears that high expression of MCT4 in the tumor stroma (the "Reverse Warburg EWffect") is specifically associated with a "lethal tumor microenvironment" (FIG. 7).

Consistent with our current observations, increased serum and tumor L-lactate is a specific marker of poor clinical outcome in variety of cancer types 61-64, and lactic acidosis is a life-threatening complication in patients with metastatic breast cancer 65-70. Thus, these previous results may have been due to L-lactate over-production in the tumor microenvironment, rather than in epithelial tumor cells.

Stromal MCT4: Implications for Treatment Stratification

Here, we also show that stromal Cav-1 can be used in combination with stromal MCT4 to further stratify the intermediate risk group, into high-risk and low-risk subgroups, effectively increasing the prognosis power of stromal Cav-1 as a biomarker (FIG. 8). Now that we believe we can unambiguously identify high-risk breast cancer patients (stromal Cav-1-0 and stromal MCT4-2), with "Reverse Warburg Effect", this new biomarker combination could be used to initiate a series of prospective clinical trials, to effectively predict prognosis and reduce mortality in this high-risk patient population.

Based on our mechanistic studies, this high-risk patient population should be more responsive to certain FDA-approved therapeutics, such as anti-oxidants (N-acetyl-cystein (NAC)), autophagy inhibitors (chloroquine and hydroxyl-chloroquine), mitochondrial "poisons" (metformin), as well as autophagy inducers (rapamycin and its derivatives)[20]. All of these therapies would uncouple anabolic cancer cells from their catabolic hosts, by interrupting energy-transfer, effectively cutting off the fuel supply of preventing cancer cells from using the fuel supply (L-lactate, ketones, and/or glutamine) (Table 7). For Examiner, they could be used synergistically, in combination with conventional therapies, or during remission after conventional therapy to prevent recurrence, or even as single agents in patients with advanced metastatic disease.

New targeted therapies would include MCT4 inhibitors to inhibit L-lactate/ketone efflux from glycolytic cancer-associated fibroblasts. MCT1/2 inhibitors may also be a rational approach, as they would likely prevent epithelial cancer from "siphoning-off" L-lactate/ketones from the MCT4(+) tumor microenvironment. MCT1 is highly expressed in epithelial tumor cells, and is involved in L-lactate/ketone uptake[29].

So, high-risk patients (defined as, stromal Cav-1-0 and stromal MCT4-2) could be selected for treatment with MCT1-inhibitors (such as, AR-C155858, AR-C117977, and AZD-3965[71, 72]) that have recently been developed by AstraZeneca, and are now undergoing Phase I/II clinical trials.

See the following MCT1 inhibitor trial-related information:

http://www.pharmaceutical-technology.com/news/news95840.html http://drugdiscoverynews.com/index.php?pg-77&articled-4235

TABLE 1

Descriptive statistics for the TN Cohort.

| Variable | N | Values |
|---|---|---|
| Age (years) | 179 | 55.5 +/− 13.7 |
| Race | 178 | |
| White | | 76% (135) |
| African American | | 24% (43) |
| Tumor size (cm) | 164 | 2.34 +/− 1.80 |
| Histologic grade | 168 | |
| 1-2 | | 26% (43) |
| 3 | | 74% (125) |
| Stage | 171 | |
| 0 | | 1% (1) |
| 1 | | 36% (62) |
| 2 | | 46% (78) |
| 3 | | 12% (21) |
| 4 | | 5% (9) |
| Lymph node status | 146 | |
| Negative | | 58% (85) |
| Positive | | 42% (61) |

Numbers in brackets are frequencies. m ± s denotes mean ± standard deviation. N denotes number of non-missing observations. Total number of subjects in this study is 181.

TABLE 2

Joint frequency distribution of stromal Cav-1 and stromal MCT4. There is evidence of a strong negative relationship between Cav-1 and MCT4 expression. The p-value is for the Fisher's exact test of independence between Cav-1 and MCT4 expression. The table includes only those records for which both Cav-1 and MCT4 are present (N = 159)

| | | MCT4 | | | | |
|---|---|---|---|---|---|---|
| | | 0 | 1 | 2 | Total | P value |
| Cav-1 | 0 | 0 | 12 | 39 | 51 | $5 \times 10^{-15}$ |
| | 1 | 8 | 29 | 13 | 50 | |
| | 2 | 24 | 31 | 3 | 58 | |
| Total | | 32 | 72 | 55 | 159 | |

TABLE 3

Hazard ratios for stromal Cav-1.

| | | Hazard Ratio | 95% Confidence Interval |
|---|---|---|---|
| Stromal Cav-1 | 0 | 14.17 | (5.53, 36.35) |
| | 1 | 4.82 | (1.78, 13.08) |
| | 2 (ref) | 1 | |

TABLE 4

Hazard ratios for stromal MCT4.

| | | Hazard Ratio | 95% Confidence Interval |
|---|---|---|---|
| Stromal MCT4 | 0 | 0.02 | (0.00, 0.16) |
| | 1 | 0.20 | (0.11, 0.35) |
| | 2 (ref) | 1 | |

TABLE 5

10 year survival by stromal MCT4 expression: Overall and conditional on stromal Cav-1 expression.

| | | Stromal MCT4 | | |
|---|---|---|---|---|
| | | MCT4 = 0 | MCT4 = 1 | MCT4 = 2 |
| Overall | 10 yr survival | 96.9% | 75.5% | 17.7% |
| | MCT4 = 0 | | $3.9 \times 10^{-4}$ | $4.2 \times 10^{-33}$ |
| | MCT4 = 1 | | | $1.5 \times 10^{-13}$ |
| Cav-1 = 1 | 10 yr survival | 87.5% | 77.9% | 0% |
| | MCT4 = 0 | | 0.50 | $7.3 \times 10^{-14}$ |
| | MCT4 = 1 | | | $2.14 \times 10^{-22}$ |

The shaded rows are the survival estimates, and the unshaded rows are the pairwise p-values testing equality of 10 year survival between strata.

TABLE 6

10 year survival by stromal Cav-1 expression: Overall and conditional on stromal MCT4 expression.

| | | Stromal Cav-1 | | |
|---|---|---|---|---|
| | | Cav-1 = 0 | Cav-1 = 1 | Cav-1 = 2 |
| Overall | 10 yr survival | 25.2% | 58.9% | 90.8% |
| | Cav-1 = 0 | | 0.001 | $5.9 \times 10^{-18}$ |
| | Cav-1 = 1 | | | $4.6 \times 10^{-4}$ |
| MCT4 = 1 | 10 yr survival | 43.8% | 77.9% | 86.7% |
| | Cav-1 = 0 | | 0.05 | 0.01 |
| | Cav-1 = 1 | | | 0.39 |

The shaded rows are the survival estimates, and the unshaded rows are the pairwise p-values testing equality of 10 year survival between strata.

TABLE 7

Candidate FDA-Approved Drugs for Targeting Two-Compartment Tumor Metabolism.

| Candidate Drugs | Predicted Mechanism(s) of Action |
|---|---|
| 1. N-Acetyl-Cysteine (NAC) | Anti-Oxidant |
| Will prevent oxidative stress in cancer-associated fibroblasts, halting autophagy in the tumor stroma, thereby cutting of the fuel supply (L-lactate, ketones, glutamine) to breast cancer cell mitochondria. | |
| 2. Hydroxy-Chloroquine* | Autophagy Inhibitor |
| Will inhibit autophagy and mitophagy in cancer-associated fibroblasts, thereby cutting off the fuel supply (L-lactate, ketones, glutamine) to breast cance cell mitochondria. | |
| 3. Metformin | Inhibitor of Mitochondrial OXPHOS (Complex I) |
| Will inhibit oxidative mitochondrial metabolism (OXPHOS) in breast cancer cells, preventing them from using L-lactate, ketones, and glutamine as mitochondrial fuels. | |
| 4. Rapamycin & Rapalogues | Autophagy Inducer(s) |
| Will induce autophagy and mitophagy in breast cancer cells, preventing them from using the available high-energy mitochondrial fuels, such as L-lactate, ketones, and glutamine. | |

*Clinically, hydroxy-chloroquine is preferred as it has less side-effects than the parent compound, chloroquine. Importantly, we have shown that NAC, chloroquine, and metformin all prevent loss of stromal Cav-1 in fibroblasts, when co-cultured with breast cancer cells.

REFERENCES

All references, including publication, patent applications, and patents, cited herein are hereby incorporated by reference to the same extent as if each reference were individually and specifically indicate to be incorporated by reference and were set forth in its entirety herein.

1. Witkiewicz A K, Dasgupta A, Sotgia F, Mercier I, Pestell R G, Sabel M, Kleer C G, Brody J R, Lisanti M P. An absence of stromal caveolin-1 expression predicts early tumor recurrence and poor clinical outcome in human breast cancers. Am J Pathol 2009; 174:2023-34.
2. Witkiewicz A K, Dasgupta A, Sammons S, Er 0, Potoczek M B, Guiles F, Sotgia F, Brody J R, Mitchell E P, Lisanti M P. Loss of stromal caveolin-1 expression predicts poor clinical outcome in triple negative and basal-like breast cancers. Cancer Biol Ther 2010; 10:135-43.
3. Witkiewicz A K, Dasgupta, Nguyen K H, Liu C, Kovatich A J, Schwartz G F, Pestell R G, Sotgia F, Rui I I, Lisant M P. Stromal caveolin-1 levels predict early DCIS progression to invasive breast cancer Cancer Biol Ther 2009; 8:1071-9.
4. Sloan E K, Ciocca D R, Pouliot N, Natoli A, Restall C, Henderson M A, Fanelli M A, Cuello-Carrion F D, Gago F E, Anderson R L. Stromal cell expression of caveolin-1 predicts outcome in breast cancer. Am J Pathol 2009; 174:2035-43.
5. Koo J S, Park S, Kim S I, Lee S, Park B W. The impact of caveolin protein expression in tumor stroma on prognosis of breast cancer. Tumour Biol 2011; 32:787-99.
6. Qian N, Ueno T, Kawaguchi-Sakita N, Kawashima M, Yoshida N, Mikami Y, Wakasa T, Shintaku M, Tsuyuki S, Inamoto T, Toi M. Prognostic significance of tumor/stromal caveolin-1 expression in breast cancer patients. Cancer Sci 2011; 102:1590-6.
7. El-Gendi S M, Mostafa M F, El-Gendi A M. Stromal Caveolin-1 Expression in Breast Carcinoma. Correlation with Early Tumor Recurrence and Clinical Outcome. Pathol Oncol Res 2012; DOI 10.1007/s12253-011-9469-5: In Press.
8. Simpkins S, Holliday D, Speirs V. The role of stromal caveolin-1 in breast cancer progression. NCRI Cancer Conference 2011; Abstract #A222:http://www.neri-.org.uk/nericonference/2011 abstracts/abstracts/A222.html.
9. Di Vizio D, Morello M, Sotgia F, Pestell R G, Freeman M R, Lisanti M P. An absence of stromal caveolin-1 is associated with advanced prostate cancer, metastatic disease and epithelial Akt activation. Cell Cycle 2009; 8:2420-4.
10. Wu K N, Queenan M, Brody J R, Potoczek M, Sotgia F, Lisanti M P, Witkiewicz A K. Loss of stromal caveolin-1 expression in malignant melanoma metastases predicts poor survival. Cell Cycle 2011; 10:4250-5.
11. Pavlides S, Whitaker-Menenes D, Castello-Cros R, Flomenberg N, Witkiewicz A K, Frank P G, Casimiro M C, Wang C, Fortina P, Addya S, Pestell R G, Martinez-Outschoorn U E, Sotgia F, Lisanti M P. The reverse Warburg effect: aerobic glycolysis in cancer associated fibroblasts and the tumor stroma. Cell Cycle 2009; 8:3984-4001.
12. Pavlides S, Tsirigos A, Vera I. Flomenberg N, Frank P G, Casimiro M C, Wang C, Fortina P, Addya S, Pestell R G, Martinez-Outschoorn U E, Sotgia F, Lisanti M P. Loss of stromal caveolin-1 leads to oxidative stress, mimics hypoxia and drives inflammation in the tumor microenvironment, conferring the "reverse Warburg effect": A transcriptional informatics analysis with validation. Cell Cycle 2010; 9.
13. Pavlides S, Tsirigos A, Migneco G, Whitaker-Menezes D, Chiavarina B, Flomenberg N, Frank P G, Casimiro M C, Wang C, Pestell R G, Martinez-Outschoorn U E, Howell A, Sotgia F, Lisanti M P. The autophagic tumor stroma model of cancer: Role of oxidative stress and ketone production in fueling tumor cell metabolism. Cell Cycle 2010; 9.
14. Trimmer C, Sotgia F, Whitaker-Menezes D, Balliet R M, Eaton G, Martinez-Outschoorn U E, Pavlides S, Howell A, Iozzo R V, Pestell R G, Scherer P E, Capozza F, Lisanti M P. Caveolin-1 and mitochondrial SOD2 (MnSOD) function as tumor suppressors in the stromal microenvironment: A new genetically tractable model for human cancer associated fibroblasts. Cancer Biol Ther 2011; 11:383-94.
15. Bonuccelli G, Whitaker-Menezes D, Castello-Cros R, Pavlides S, Pestell R G, Fatatis A, Witkiewicz A K, Vander Heiden M G, Migneco G, Chiavarina B, Frank P G, Capozza F, Flomenberg N, Martinez-Outschoorn U E, Sotgia F, Lisanti M P. The reverse Warburg effect: Glycolysis inhibitor prevent the tumor promoting effects of caveolin-1 deficient cancer associated fibroblasts. Cell Cycle 2010; 9.
16. Witkiewicz A K, Kline J, Queenan M, Brody J R, Tsirigos A, Bilal E, Pavlides S, Ertel A, Sotgia F, Lisanti M P. Molecular profiling of a lethal tumor microenvironment, as defined by stromal caveolin-1 status in breast cancers. Cell Cycle 2011; 10: 1794-809.
17. Martinez-Outschoorn U E, Pestell R G, Howell A, Nagajyothi F, Machado F S, Tanowitz H B, Sotgia F, Lisanti M P. Energy transfer in "parasitic" cancer metabolism: Mitochondria are the powerhouse and Achilles' heel of tumor cells. Cell Cycle 2011; 10:4208-16.
18. Martinez-Outschoorn U E, Sotgia F, Lisanti M P. Power Surge: Supporting Cells "Fuel" Cancer Cell Mitochondria. Cell Metab 2012; 15:4-5.
19. Martinez-Outschoorn U E, Pavlides S, Howell A, Pestell R G, Tanowitz H B, Sotgia F, Lisanti M P. Stromal-epithelial metabolic coupling in cancer: integrating autophagy and metabolism in the tumor microenvironment. Int J Biochem Cell Biol 2011; 43:1045-51.
20. Martinez-Outschoorn U E, Whitaker-Menezes D, Pavlides S, Chiavarina B, Bonuccelli G, Casey T, Tsirigos A, Migneco G, Witkiewicz A, Balliet R, Mercier I, Wang C, Flomenberg N, Howell A, Lin Z, Caro J, Pestell R G, Sotgia F, Lisanti M P. The autophagic tumor stroma model of cancer or "battery-operated tumor growth": A simple solution to the autophagy paradox. Cell Cycle 2010; 9:4297-306.
21. Sotgia F, Martinez-Outschoorn U E, Howell A, Pestell R G, Pavlides S, Lisanti M P. Caveolin-1 and Cancer Metabolism in the Tumor Microenvironment: Markers, Models, and Mechanisms. Annu Rev Pathol 2012; 7:423-67.
22. Sotgia F, Martinez-Outschoorn U E, Pavlides S, Howell A, Pestell R G, Lisanti M P. Understanding the Warburg effect and the prognostic value of stromal caveolin-1 as a marker of a lethal tumor microenvironment. Breast Cancer Res 2011; 13:213.
23. Pavlides S, Vera I, Gandara R, Sneddon S, Pestell R G, Mercier I, Martinez-Outschoorn U E, Whitaker-Menezes D, Howell A, Sotgia F, Lisanti M P. Warburg Meets Autophagy: Cancer-Associated Fibroblasts Accelerate Tumor Growth and Metastasis via Oxidative Stress, Mitophagy, and Aerobic Glycolysis. Antioxid Redox Signal 2011.
24. Ertel A, Tsirigos A, Whitaker-Menezes D, Birbe R C, Pavlides S, Martinez-Outschoorn U E, Pestell R G, Howell A, Sotgia F, Lisanti M P. Is cancer a metabolic rebellion against host aging? In the quest for immortality, tumor cells try to save themselves by boosting mitochondrial metabolism. Cell Cycle 2012; 11:253-63.
25. Martinez-Outschoorn U E, Pavlides S, Whitaker-Menezes D, Daumer K M, Milliman J N, Chiavarina B, Migneco G, Witkiewicz A K, Martinez-Cantarin M P, Flomenberg N, Howell A, Pestell R G, Lisanti M P, Sotgia F. Tumor cells induce the cancer associated fibroblast phenotype via caveolin-1 degradation: Implications for breast cancer and DCIS therapy with autophagy inhibitors. Cell Cycle 2010; 9:2423-33.
26. Martinez-Outschoorn U E, Balliet R M, Rivadeneira D B, Chiavarina B, Pavlides S, Wang C, Whitaker-Menezes D, Daumer K M, Lin Z, Witkiewicz A K, Flomenberg N, Howell A, Pestell R G, Knudsen E S, Sotgia F, Lisanti M P. Oxidative stress in cancer associated fibroblasts drives tumor-stroma co-evolution: A new paradigm for understanding tumor metabolism, the field effect and genomic instability in cancer cells. Cell Cycle 2010; 9:3256-76.
27. Martinez-Outschoorn U E, Trimmer C, Lin Z, Whitaker-Menezes D, Chiavarina B, Zhou J, Wang C, Pavlides S, Martinez-Cantarin M P, Capozza F, Witkiewicz A K, Flomenberg N, Howell A, Pestell R G, Caro J, Lisanti M P, Sotgia F. Autophagy in cancer associated fibroblasts promotes tumor cell survival: Role of hypoxia, HIF1 induction and NFkappaB activation in the tumor stromal microenvironment. Cell Cycle 2010; 9:3515-33.
28. Martinez-Outschoorn U E, Lin Z, Trimmer C, Flomenberg N, Wang C, Pavlides S, Pestell R G, Howell A, Sotgia F, Lisanti M P. Cancer cells metabolically "fertilize" the tumor microenvironment with hydrogen peroxide, driving the Warburg effect: Implications for PET imaging of human tumors. Cell Cycle 2011; 10:2504-20.
29. Whitaker-Menezes D, Martinez-Outschoorn U E, Lin Z, Ertel A, Flomenberg N, Witkiewicz A K, Birbe R C, Howell A, Pavlides S, Gandara R, Pestell R G, Sotgia F, Philp N J, Lisanti M P. Evidence for a stromal-epithelial "lactate shuttle" in human tumors: MCT4 is a marker of oxidative stress in cancer-associated fibroblasts. Cell Cycle 2011; 10:1772-83.
30. Gallagher S M, Castorino J J, Wang D, Philp N J. Monocarboxylate transporter 4 regulates maturation and trafficking of CD147 to the plasma membrane in the metastatic breast cancer cell line MDA-MB-231. Cancer Res 2007; 67:4182-9.
31. Pertega-Gomes N, Vizcaino J R, Miranda-Goncalves V, Pinheiro C, Silva J, Pereira H, Monteiro P, Henrique R, Reis R M, Lopes C, Baltazar F. Monocarboxylate transporter 4 (MCT4) and CD147 overexpression is associated with poor prognosis in prostate cancer. BMC Cancer 2011; 11:312.
32. R-Development-Core-Team. R: A language and environment for statistical computing. R Foundation for Statistical Computing, Vienna, Austria 2011; ISBN 3-900051-07-0.
33. Themeau T, original Splus→R port by T. Lumley. Survival: Survival analysis, including penalised likelihood. R package version 236-9 2011; http://CRAN.R-project.org/package-survival.

34. Paget S. The distribution of secondary growths in cancer of the breast. 1889. Cancer Metastasis Rev 1989; 8:98-101.
35. Hart I R. 'Seed and soil' revisited: mechanisms of site-specific metastasis. Cancer Metastasis Rev 1982; 1:5-16.
36. Hart I R, Fidler I J. Role of organ selectivity in the determination of metastatic patterns of B16 melanoma. Cancer Res 1980; 40:2281-7.
37. Lisanti M P, Martinez-Outschoorn U E, Lin Z, Pavlides S, Whitaker-Menezes D, Pestell R G, Howell A, Sotgia F. Hydrogen peroxide fuels aging, inflammation, cancer metabolism and metastasis: the seed and soil also needs "fertilizer". Cell Cycle 2011; 10:2440-9.
38. Lisanti M P, Martinez-Outschoorn U E, Pavlides S, Whitaker-Menezes D, Pestell R G, Howell A, Sotgia F. Accelerated aging in the tumor microenvironment: connecting aging, inflammation and cancer metabolism with personalized medicine. Cell Cycle 2011; 10:2059-63.
39. Martinez-Outschoorn U E, Whitaker-Menezes D, Lin Z, Flomenberg N, Howell A, Pestell R G, Lisanti M P, Sotgia F. Cytokine production and inflammation drive autophagy in the tumor microenvironment: role of stromal caveolin-1 as a key regulator. Cell Cycle 2011; 10:1784-93.
40. Martinez-Outschoorn U E, Prisco M, Ertel A, Tsirigos A, Lin Z, Pavlides S, Wang C, Flomenberg N, Knudsen E S, Howell A, Pestell R G, Sotgia F, Lisanti M P. Ketones and lactate increase cancer cell "stemness," driving recurrence, metastasis and poor clinical outcome in breast cancer: achieving personalized medicine via Metabolo-Genomics. Cell Cycle 2011; 10:1271-86.
41. Martinez-Outschoorn U E, Goldberg A, Lin Z, Ko Y H, Flomenberg N, Wang C, Pavlides S, Pestell R G, Howell A, Sotgia F, Lisanti M P. Anti-estrogen resistance in breast cancer is induced by the tumor microenvironment and can be overcome by inhibiting mitochondrial function in epithelial cancer cells. Cancer Biol Ther 2011; 12:924-38.
42. Martinez-Outschoorn U E, Lin Z, Ko Y H, Goldberg A F, Flomenberg N, Wang C, Pavlides S, Pestell R G, Howell A, Sotgia F, Lisanti M P. Understanding the metabolic basis of drug resistance: Therapeutic induction of the Warburg effect kills cancer cells. Cell Cycle 2011; 10:2521-8.
43. Whitaker-Menezes D, Martinez-Outschoorn U E, Flomenberg N, Birbe R C, Witkiewicz A K, Howell A, Pavlides S, Tsirigos A, Ertel A, Pestell R G, Broda P, Minetti C, Lisanti M P, Sotgia F. Hyperactivation of Oxidative Mitochondrial Metabolism in Epithelial Cancer Cells In Situ: Visualizing the Therapeutic Effects of Metformin in Tumor Tissue. Cell Cycle 2011; 10: 4047-64.
44. Chiavarina B, Whitaker-Menezes D, Martinez-Outschoom U E, Witkiewicz A K, Birbe R C, Howell A, Pestell R G, Smith J, Daniel R, Sotgia F, Lisanti M P. Pyruvate kinase expression (PKM1 and PKM2) in cancer-associated fibroblasts drives stromal nutrient production and tumor growth. Cancer Biol Ther 2011; 12:1101-13.
45. Ko Y H, Lin Z, Flomenberg N, Pestell R G, Howell A, Sotgia F, Lisanti M P, Martinez-Outschoorn U E. Glutamine fuels a vicious cycle of autophagy in the tumor stroma and oxidative mitochondrial metabolism in epithelial cancer cells: Implications for preventing chemotherapy resistance. Cancer Biol Ther 2011; 12: 1085-97.
46. Balliet R M, Capparelli C, Guido C, Pestell T G, Martinez-Outschoorn U E, Lin Z, Whitaker-Menezes D, Chiavarina B., Pestell R G, Howell A, Sotgia F, Lisanti M P. Mitochondrial oxidative stress in cancer-associated fibroblasts drives lactate production, promoting breast cancer tumor growth: Understanding the aging and cancer connection. Cell Cycle 2011; 10:4065-73.
47. Chiavarina B, Whitaker-Menezes D, Migneco G, Martinez-Outschoorn U E, Pavlides S, Howell A, Tanowitz H B, Casimiro M C, Wang C, Pestell R G, Grieshaber P, Caro J, Sotgia F, Lisanti M P. HIF1-alpha functions as a tumor promoter in cancer associated fibroblasts, and as a tumor suppressor in breast cancer cells: Autophagy drives compartment-specific oncogenesis. Cell Cycle 2010; 9.
48. Bergersen L H. Is lactate food for neurons? Comparison of monocarboxylate transporter subtypes in brain and muscle. Neuroscience 2007; 145:11-9.
49. Pierre K, Pellerin L. Monocarboxylate transporters in the central nervous system: distribution, regulation and function. J Neurochem 2005; 94: 1-14.
50. Dimmer K S, Friedrich B, Lang F, Deitmer J W, Broer S. The low-affinity monocarboxylate transporter MCT4 is adapted to the export of lactate in highly glycolytic cells. Biochem J 2000; 350 Pt 1:219-27.
51. Ullah M S, Davies A J, Halestrap A P. The plasma membrane lactate transporter MCT4, but not MCT1, is up-regulated by hypoxia through a HIF-1alpha-dependent mechanism. J Biol Chem 2006; 281:9030-7.
52. Brooks G A. Lactate shuttles in nature. Biochem Soc Trans 2002; 30:258-64.
53. Brooks G A. Current concepts in lactate exchange. Med Sci Sports Exerc 1991: 23:895-906.
54. Magistretti P J. Neuron-glia metabolic coupling and plasticity. J Exp Biol 2006; 209:2304-11.
55. Magistretti P J. Role of glutamate in neuron-glia metabolic coupling. Am J Clin Nutr 2009; 90:875 S-80S.
56. Magistretti P J, Pellerin L. The contribution of astrocytes to the 18F-2-deoxyglucose signal in PET activation studies. Mol Psychiatry 1996; 1:445-52.
57. Warburg O. On respiratory impairment in cancer cells. Science 1956; 124:269-70.
58. Warburg O. On the origin of cancer cells. Science 1956; 123:309-14.
59. Vander Heiden M G, Cantley L C, Thompson C B. Understanding the Warburg effect: the metabolic requirements of cell proliferation. Science 2009; 324:1029-33.
60. Zu X L, Guppy M. Cancer metabolism: facts, fantasy, and fiction. Biochem Biophys Res Commun 2004; 313: 45-65.
61. Brizel D M, Schroeder T, Scher R L, Walenta S, Clough R W, Dewhirst M W, Mueller-Klieser W. Elevated tumor lactate concentrations predict for an increased risk of metastases in head-and-neck cancer. Int J Radiat Oncol Biol Phys 2001; 51:349-53.
62. Walenta S, Wetterling M, Lehrke M, Schwickert G, Sundfor K, Rofstad E K, Mueller-Klieser W. High lactate levels predict likelihood of metastases, tumor recurrence, and restricted patient survival in human cervical cancers. Cancer Res 2000; 60:916-21.
63. Walenta S, Mueller-Klieser W F. Lactate: mirror and motor of tumor malignancy. Semin Radiat Oncol 2004; 14:267-74.
64. Walenta S, Salameh A, Lyng H, Evensen J F, Mitze M, Rofstad E K, Mueller-Klieser W. Correlation of high lactate levels in head and neck tumors with incidence of metastasis. Am J Pathol 1997; 150:4 9-15.
65. Sculier J P, Nicaise C, Klastersky J. Lactic acidosis: a metabolic complication of extensive metastatic cancer. Eur J Cancer Clin Oncol 1983; 19:597-601.
66. Varanasi U R, Carr B, Simpson D P. Lactic acidosis associated with metastatic breast carcinoma. Cancer Treat Rep 1980; 64:1283-5.

67. McConnell A A, Parfitt V L, Walker P R. An unusual case of shock in a young woman. Postgrad Med J 1989; 65:120.
68. Warner E. Type B lactic acidosis and metastatic breast cancer. Breast Cancer Res Treat 1992; 24:75-9.
69. Evans T R, Stein R C, Ford H T, Gazet J C, Chamberlain G V, Coombes R C. Lactic acidosis. A presentation of metastatic breast cancer arising in pregnancy. Cancer 1992; 69:453-6.
70. Cheng J C, Esparza S D, Knez V M, Sakamoto K M, Moore T B. Severe lactic acidosis in a 14-year-old female with metastatic undifferentiated carcinoma of unknown primary. J Pediatr Hematol Oncol 2004; 26:780-2.
71. Bueno V, Binet I, Steger U, Bundick R, Ferguson D, Murray C, Donald D, Wood K. The specific monocarboxylate transporter (MCT1) inhibitor, AR-C117977, a novel immunosuppressant, prolongs allograft survival in the mouse. Transplantation 2007; 84:1204-7.
72. Ovens M J, Davies A J, Wilson M C, Murray C M, Halestrap A P. AR-C155858 is a potent inhibitor of monocarboxylate transporters MCT1 and MCT2 that binds to an intracellular site involving transmembrane helices 7-10. Biochem J 2010; 425:523-30.
73. PCT Publication No. WO2010/089580, published Aug. 12, 2010.
74. PCT Publication No. WO2004/065394, published Aug. 5, 2004.

The invention claimed is:
1. A method for treating a triple negative breast cancer/tumor whose stromal component expresses the MCT4 protein in a patient, comprising:
   (a) obtaining a stromal breast tissue sample from said patient;
   (b) determining the expression level of stromal MCT4 protein in said stromal breast tissue sample by staining the stromal cells for MCT4 expression;
   (c) determining the expression level of stromal Cav-1 protein in said sample of cancer/tumor tissue by staining the stromal tissues for Cav-1 expression; and
   (d) diagnosing the patient with a high risk cancer by scoring the stained stromal cells, said diagnosis being confirmed wherein more than 30% of said stromal cells are stained in a sample for MCT4 expression and wherein no straining of the stromal cells is identified for Cav-1 expression; and
   (e) administering to said diagnosed patient with a high risk cancer, an MCT protein inhibitor wherein the MCT protein inhibitor is selected from the group consisting of AR-C15858, AR C117977, and AZD-3965, wherein AZD-3965, AR C155858 and AR C117977 are represented by the following formulas:

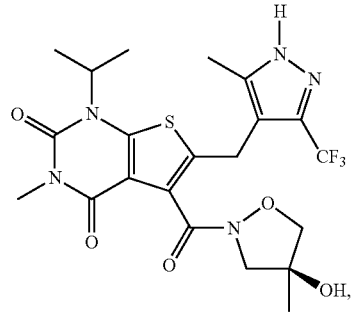
AZD-3965

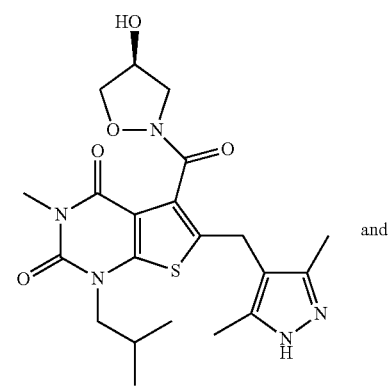
AR-C155858
and

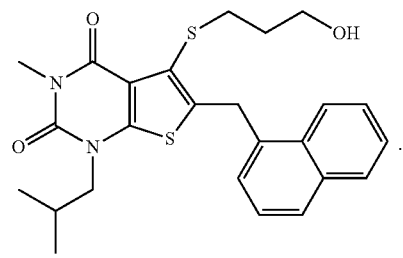
AR C117977

2. The method of claim 1, wherein the mode of administration of said compound is inhalation, oral, intravenous, sublingual, ocular, transdermal, rectal, vaginal, topical, intramuscular, intraperitoneal, epidural, subcutaneous, buccal, or nasal.

* * * * *